US008509928B2

(12) United States Patent
Abate et al.

(10) Patent No.: US 8,509,928 B2
(45) Date of Patent: Aug. 13, 2013

(54) METHOD AND APPARATUS FOR PRODUCING STATIONARY INTENSE WAVE FIELDS OF ARBITRARY SHAPE

(75) Inventors: Valerio Abate, Saronno (IT); Cesar Augusto Dartora, Erechim (BR); Hugo Enrique Hernàndez Figueroa, Sao Paolo (BR); Marco Mattiuzzi, Grassina Bagno a Ripoli (IT); Kleber Zuza Nobrega, Fortaleza-Ceara (BR); Michel Zamboni Rached, Sao Paolo (BR); Erasmo Recami, Mozzo (IT)

(73) Assignee: Bracco Imaging S.P.A., Milan (IT)

( * ) Notice: Subject to any disclaimer, the term of this patent is extended or adjusted under 35 U.S.C. 154(b) by 1355 days.

(21) Appl. No.: 11/569,460

(22) PCT Filed: May 23, 2005

(86) PCT No.: PCT/EP2005/052352
§ 371 (c)(1),
(2), (4) Date: Apr. 2, 2009

(87) PCT Pub. No.: WO2005/119647
PCT Pub. Date: Dec. 15, 2005

(65) Prior Publication Data
US 2011/0100880 A1    May 5, 2011

(30) Foreign Application Priority Data
May 27, 2004  (EP) .................................... 04425387

(51) Int. Cl.
*G06F 17/00*    (2006.01)
*H04B 3/04*    (2006.01)

(52) U.S. Cl.
USPC ............................................... 700/90; 333/20

(58) Field of Classification Search
USPC ........ 700/90; 209/1; 181/142, 246; 216/52; 250/251, 503.1; 359/9, 896; 367/8; 378/36; 372/2; 333/20
See application file for complete search history.

(56) References Cited

U.S. PATENT DOCUMENTS

| 5,245,619 A | * | 9/1993 | Kronberg | 372/32 |
| 5,370,643 A | * | 12/1994 | Krivoshlykov et al. | 606/16 |
| 6,016,223 A | * | 1/2000 | Suzuki et al. | 359/577 |
| 7,046,703 B2 | * | 5/2006 | Rice | 372/2 |

* cited by examiner

*Primary Examiner* — Charles Kasenge
(74) *Attorney, Agent, or Firm* — Themis Law

(57) ABSTRACT

Method for producing a stationary wave field of arbitrary shape comprising the steps of defining at least one volume being limited in the direction of the axis of propagation of a beam, of the type $0 \leq z \leq L$; defining an intensity pattern within the said region $0 \leq z \leq L$ by a function $F(z)$, describing the said localized and stationary intensity pattern, which is approximated by means of a Fourier expansion or by a similar expansion in terms of (trigonometric) orthogonal functions; providing a generic superposition of Bessel or other beams highly transversally confined; calculating the maximum number of superimposed Bessel beams the amplitudes, the phase velocities and the relative phases of each Bessel beam of the superposition, and the transverse and longitudinal wavenumbers of each Bessel beam of the superposition.

33 Claims, 21 Drawing Sheets

METHOD AND APPARATUS FOR PRODUCING STATIONARY INTENSE WAVE FIELDS OF ARBITRARY SHAPE

CROSS REFERENCE TO RELATED APPLICATIONS

This application is the United States national stage filing of corresponding international application number PCT/EP2005/052352 filed on May 23, 2005, which claims priority to and benefit of European application number 04425387.0, filed May 27, 2004, each of which is hereby incorporated herein by reference.

BACKGROUND OF THE INVENTION

The invention relates to a method for producing a stationary (intense) wave field of arbitrary longitudinal shape and high transverse localization.

Since many years it has been known that suitable frequency superpositions of Bessel beams, with the same phase velocity, yield localized wave pulses. Such pulses possessed the surprising characteristic of resisting the diffraction effects during their propagation.

In U.S. Pat. No. 5,081,995 Lu has shown that it is possible to produce a non-diffracting series of (acoustic) pulses by using a piezoelectric transducer consisting in a series of rings. The piezoelectric transducer produces ultrasonic pulses used to increase the field resolution. The use of annular transducers is common, since axial symmetry is convenient for reducing diffraction in the generated wave fields.

Optical laser-light Bessel beams have been generated by Durnin et al. with a very simple experimental apparatus comprising a laser beam source, an annular slit, and a lens. A gaussian beam generated by the laser beam is transformed into a Bessel beam which is highly non-diffracting.

It would be of high technical relevance if a wave field could be generated, possessing not only a highly non-diffracting behaviour (i.e., being radially confined relatively to the direction of propagation), but also being confined within a predetermined space-region limited both in its direction of propagation and in its transverse direction. In this situation, inside the interval 0<=z<=L, at least one 3-dimensional space-regions can be defined, having a predetermined size $L_1$<=z<=$L_2$ within the said interval 0<=z<=L, so that the field is therein confined, and negligible outside it. Of course, since the method uses Fourier-type transformations, the same pattern a priori gets repeated inside each successive interval L<=z<=2L, etc., unless the depth-field of each Bessel beam entering the superposition considered in the disclosed method is chosen to be not much gratee than L.

Document QING CAO ET AL: "Axially symmetric on-axis flap-top beam" JOURNAL OF THE OPTICAL SOCIETY OF AMERICA A (OPTICS, IMAGE SCIENCE AND VISION) OPT. SOC. AMERICA USA, vol. 17, no. 3, March 2000 (2000-03), pages 447-455, XP002305056 ISSN:0740-3232, describes a method for building a flat-top beam which is a square-shaped wave field having a width L. The starting point of the disclosed method is the Fourier integral of the Fourier Transform $$\varphi(S) = \int_{-\infty}^{\infty} \sqrt{I_g(o, z)} \exp(i2\pi Sz) dz$$

and its inverse function $$\int_{-\infty}^{-S_i} \varphi(S) \exp(-i2\pi Sz) dS.$$

This method making use of the traditional Fourier Integrals the disclosed method need to use values of S which runs also over negative values.

Furthermore the method disclosed in the above mentioned publication uses also a Fourier-Bessel transform. As it is well known Bessel beams constitute a base which can be used to express any function. In the disclosed method integrals running over positive values of S only since the Fourier-Bessel transform cannot accept negative values of the integration variable and integrals running also over negative values of the integration variable are mixed together. This approximation is justified as mentioned in the document only if the shift-term S could tend to infinity. However the paraxial approximation assumed in the above cited document is known as hold only for small values of S. Thus the method disclosed in the above cited publication is limited to configurations of the beam shape and dimensions for which the paraxial approximation is valid. For cases for which the paraxial condition is not met the authors are obliged to carry out numerical simulations. The approximate numerical simulation taught in the above publication aims only to the production of a flat-top beam and the document does not teach how to evaluate amplitudes and phases of the Bessel beams by a closed-form equation and not even by general numerical procedures. Only nan hope of generalisation of the disclosed approach is expressed by the authors.

Thus principally due to the fact that the disclosed method according to the above publication is limited by the role of the negative values of S and by the condition of the paraxial approximation this disclosed method does not allow a general treatment which is based on exact analytical equations which allow a complete control of all the parameters entering into play and of their experimental effects for producing in a simple way and without any approximation a stationary localized wave-field with an a-priori determined arbitrary shape.

A first target of the present invention is to provide a method for generating spatially confined stationary wave fields with any arbitrary (longitudinal) shape in correspondence with a segment of the type $0 \leq z \leq L$, quantity L being a periodicity interval which overcomes the drawbacks of the known methods.

A second aim is to provide a method for producing a source which generates the above-said spatially confined stationary wave field.

A further object of the present invention is to provide for an apparatus for generating a spatially confined stationary wave field.

SUMMARY OF THE INVENTION

The invention is based on the fact that suitable superpositions of Bessel beams, can yield stationary wave fields with high transverse localization, and with an arbitrary longitudinal shape. These superpositions of Bessel beams are particularly suitable when they have the same frequency. They are new solutions of the wave equation, and may be called "Frozen Waves" (FWs). They are created with any arbitrary shape inside a spatial region corresponding to a longitudinal segment of the type $0 \leq z \leq L$, and their general "envelope" does not propagate. Moreover, their shape can be such that the stationary field is concentrated only within one or more (small) portions defined herein as sub-envelopes, L−1≦z≦L−2 (of the interval 0≦z≦L), while a negligible field is expected to exist before or after the said envelope or sub-envelopes of the stationary field. Inside the said envelope or sub-envelopes a plane carrier wave is propagating, as it will be disclosed with greater detail in the following description; while the said envelope or sub-envelopes remain stationary According to the invention, other eigenfunctions of the transverse laplacian operator can be used different from Bessel beams. For instance, stationary fields (FWs) can be obtained by the superpositions furnished by the disclosed method, provided that the said eigenfunctions yield a constant value (the same for all of them) along the z-axis. In such a case, the method allows defining a Fourier series for $\alpha=0$ with the same coefficients $A_n$ furnished by the method in the Bessel Beams case.

As it will become evident form the following description, such waves can be used in a great variety of applications, ranging from optical or electromagnetic tweezers to laser-type surgery and optical or ultrasound lancets, from microlithography to ultrasound or electromagnetic thermo-therapy of tumors, from jamming electromagnetic regions (balls) to a new kind of effective holography, from ultrasound kidney stone fragmentation to other ultrasound applications, etc.

The present invention refers to a method for producing a stationary localized wave field with an a-priori predetermined arbitrary longitudinal shape, inside a periodicity interval $0 \leq z \leq L$, and with high transverse localization, and the apparatuses accordingly designed. Namely, from a general point of view, this invention provides a method for producing a stationary localized wave field of an a-priori predetermined arbitrary shape, comprising the following steps:

a) defining at least a volume being limited in the direction of the axis z of propagation of a beam, along a certain longitudinal interval $0 \leq z \leq L$;

b) defining a priori within the said longitudinal interval an intensity pattern $|F(z)|^2$ describing the desired localized and stationary wave field which function F(z) is represented by means of a discrete Fourier Series or by a similar expansion in terms of (trigonometric) orthogonal functions;

c) providing a discrete, generic superposition of Bessel beams or other highly transversally confined beams;

d) calculating the maximum allowed number of Bessel beams to be superposed;

e) calculating the amplitudes, and the phase velocities and the transverse and longitudinal wavenumbers of each Bessel beam of the superposition, needed to obtain the predefined STATIONARY intensity pattern (within the predefined longitudinal interval);

f) recognizing and controlling the effect of each of the said parameters under point e) for controlling the longitudinal shape of the stationary localized wave field.

According to the present method also a partial control of the transversal shape of the stationary wave field is carried out by superposing for instance high order Bessel beams.

Thanks to the fact that the above method is based on exact analytical equations the method according to the invention allows a complete control of all parameters entering into play and of their experimental effects for producing in a simple way and without any approximation a stationary localized wave field with an a-priori predetermined arbitrary shape. The method according to the invention allows to exercise a complete control of the longitudinal shape and at least a partial control of the transverse shape of the stationary wavefield.

The method according to the invention has the great advantage that it can be translated in a experimental device with which each relevant parameter for controlling the longitudinal and transverse shape of the stationary wave field can be influenced by simple settings of the constructive aspects of the said device.

Once a shape is chosen the method according to the present invention allows to evaluate a priori the amplitude, the phase velocity, the relative phases and the transverse and longitudinal wave numbers of each Bessel beam of the superposition, simultaneously recognizing and controlling the effect of each one of the parameters entering into play in order to obtain a total control of the longitudinal shape of the stationary wave field and by superposing high order Bessel beams even a partial control of the transverse shape of the stationary wave field.

The method requires to fix the volume of space wherein the stationary wave field has to be confined, and the stationary field itself by means of a trigonometric series, and then to define amplitude, and the other parameters (velocity or axicon angle, and phase) of each single Bessel beams entering the mentioned superposition of Bessel beams which provides the mathematical description of the desired stationary wave field. No limitation exists relatively to the kind of the considered waves. So the method associated with this invention can be applied to any kind of waves, like electromagnetic waves, acoustic waves (including sysmic or geophysical waves, and in general mechanical waves), and also gravitational waves, and so on.

In a particular embodiment of the method according to the present invention the method considers only the superposition of Bessel beams having the same frequency.

Nevertheless also a superposition of Bessel beams having different frequencies within a certain frequency bandwith or a superposition of Bessel beams which pulsed can lead to a STATIONARY (intense) wave field Within a part of the present invention, a method for producing a source, which is suitable for generating such stationary and spatially confined wave fields, is also suggested.

In its general definition, the mentioned method for producing a source comprises the following steps:

providing one source for a single Bessel beam;

generating an array of many (more than one) of the said sources of Bessel beams;

configuring each source, of the said array of Bessel beam sources, according to amplitude, phase, longitudinal and transverse wavenumbers, and relative phase of each one of the Bessel beams of the superposition for method in order to yield the stationary wave field described above.

As seen above, the proposed method allows designing, once predefined the desired behaviour of the field, the transducers able to produce such a field with a very high approximation (limited by the number of the said Bessel beam sources, which cannot be more than 2N+1, where N is the maximum number of Bessel beams entering the superposition considered by the present invention. Indeed, the method is applied by suitably superposing Bessel beams and particularly, but not exclusively Bessel beams of the same frequency, and calculating relative phase and amplitude and wavenumbers of each of the N Bessel beams entering the desired superposition.

The invention provides also several embodiments of different devices and several methods applying the above-mentioned localized stationary wave fields, which are described in greater detail in the following description and in the annexed claims.

Detailed Method for Generating a Localized Stationary Wave Field According to the Invention Let us start from the basic Bessel beam solution (with axial symmetry) of the wave equation:

$$\psi(\rho, z - c/\cos\theta\, t) = J_0\left(\frac{\omega}{c}\sin\theta\rho\right)e^{i\frac{\omega\cos\theta}{c}\left(z-\frac{c}{\cos\theta}t\right)} \quad (1)$$

On using the usual variables ($\omega$, $\beta$, $k_\rho$), where $\beta$e $k_\rho$ are the longitudinal and transverse wavenumbers, and $\omega = c\beta/\cos\theta$, the Bessel beam writes $$\psi(\rho, z, t) = J_0(k_\rho\rho)e^{i\beta z}e^{-i\omega t} \quad (2)$$

where $$k_\rho^2 = \frac{\omega^2}{c^2} - \beta^2 \geq 0 \quad (3)$$

and $$\frac{\omega}{\beta} > 0 \quad (4)$$

The conditions $\omega/\beta > 0$ and $k_\rho^2 \geq 0$ ensure forward propagation, with no evanescent waves, and physical behaviour to the Bessel function $J_o$ respectively. In the case of electromagnetic waves, quantity c represents the ordinary speed of light in vacuum.

Now, let us consider the following superposition of Bessel beams with the same frequency $\omega_0$:

$$\Psi(\rho, z, t) = e^{-i\omega_0 t} \sum_{n=-N}^{N} A_n J_0(k_{\rho n}\rho) e^{i\beta_n z} \quad (5)$$

where n are integer numbers, $A_n$ are constant coefficients, and $\beta_n$, $k_{\rho n}$ are the longitudinal and transverse wavenumbers (still to be determined), respectively; where, for each n, the parameters ($\omega_0$, $k_{\rho n}$, $\beta_n$) must satisfy Eq. (3).

Because of conditions (3) and (4), we must have $$0 \leq \beta_n \leq \frac{\omega_0}{c} \quad (6)$$

Now, our goal is using Eq. (5) to obtain a predetermined longitudinal intensity pattern within the interval $0 \leq z \leq L$.

Let us suppose that the desired pattern in the interval $0 \leq z \leq L$ is given by a function F(z). We know that in that interval we can expand function F in a Fourier series $$F(z) = \sum_{m=-\infty}^{\infty} B_m e^{i\frac{2\pi}{L}mz} \quad (7)$$

where $$B_m = \frac{1}{L}\int_0^L F(z) e^{-i\frac{2\pi}{L}mz} dz. \quad (8)$$

It would be natural to use $\beta_n = 2\pi n/L$ in Eq. (5), with $A_n = B_n$. HOWEVER this choice would imply negative values of $\beta_n$ (backward waves), what is forbidden by our condition (4), because $\omega_0$ is obviously positive.

To overcome this problem we write $\beta_n$ as:

$$\beta_n = Q + \frac{2\pi}{L}n \quad (9)$$

where Q>0 is a value chosen depending on the conditions of the given experimental situation. According to Eq. (6), we have $$0 \leq Q \pm \frac{2\pi}{L}N \leq \frac{\omega_0}{c} \quad (10)$$

The in equation (10) determines the maximum value of n, that we call N, once we have chosen Q, L and $\omega_0$. in this way, to obtain a longitudinal pattern of intensity approximately equal to the desired one, F(z), in the interval $0 \leq z \leq L$, the solution (5) should be written as:

$$\Psi(\rho = 0, z, t) = e^{-i\omega_0 t} e^{iQz} \sum_{n=-N}^{N} A_n e^{i\frac{2\pi}{L}nz} \quad (11)$$

with $$A_n = \frac{1}{L}\int_0^L F(z) e^{-i\frac{2\pi}{L}nz} dz \quad (12)$$

Obviously, we get only an approximation of the desired longitudinal pattern because the trigonometric series (11) has been truncated. The number of terms is defined, once the values of Q, L and $\omega_0$ are chosen.

When $\rho \neq 0$, $\Psi(\rho, z, t)$ is $$\Psi(\rho, z, t) = e^{-i\omega_0 t} e^{iQz} \sum_{n=-N}^{N} A_n J_0(k_{\rho n}\rho) e^{i\frac{2\pi}{L}nz} \quad (13)$$

with $$k_{\rho n}^2 = \omega_0^2 - \left(Q + \frac{2\pi n}{L}\right)^2 \quad (14)$$

The coefficients $A_n$ will give the amplitudes and the relative phases of each Bessel beam in the superposition.

Because we are adding together zero order Bessel functions, we can expect a high field concentration around $\rho = 0$.

DETAILED DESCRIPTION OF THE DRAWINGS

Examples of the Application of the Method

In this section we shall give two examples of the theoretical method according to the present invention for constructing localized stationary wave fields the method for obtaining said localized stationary wave field being already described above.

For completeness' sake, let us notice that the method provides in general the approximated representation of the desired confined stationary wave field by means of a Fourier expansion (or a Fourier-Bessel expansion when α is different from zero). This expansion can be of a kind more general than Fourier's. Although the examples use a Fourier series, it is important to notice that no limitation is set to the expansion or to the series to be used for approximating the desired spatially confined stationary wave field, provided that it is a trigonometric expansion.

The two following examples are brought hereinafter with numeric details.

First Case:

Let us suppose that we want an optical wave field with $\lambda=0.632$ μm ($\omega_0=2.98*10^{15}$ Hz), whose longitudinal pattern (on its axis) in the range $0 \leq z \leq 0.5$ m is a step function with centre located at z=0.25 m and with width Δz=0.1 m. In other words, the desired function is given by:

$$F(z)=H(z-0.2)-H(z-0.3) \quad (15)$$

where H(.) is the step function.

Figure 1:
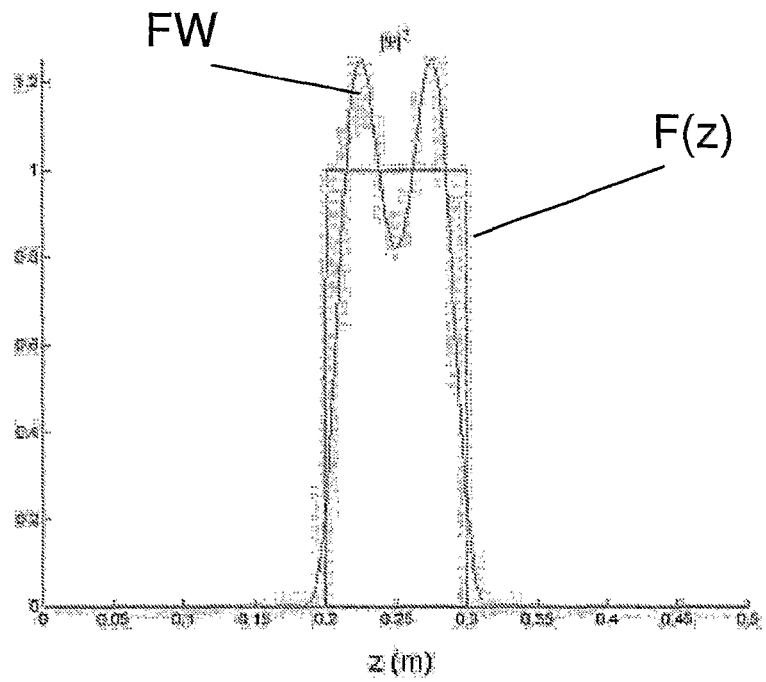
FIG. 1 shows a comparison between the intensity of the desired longitudinal function F(z) and that of the stationary wave field FW ("Frozen Wave"), $\Psi(\rho=0, z, t)$, obtained from Eq. (11)

With this, we can calculate the coefficients $A_n$, on inserting Eq. (15) into Eq. (12), and use them in the superposition given by our Eq. (13). Let us choose in this case Q=0.9999 $\omega_0$/c; this choice allows a maximum value for n given by N=79 (we can see this from Eq. (10)). However, we are not obliged to use N=79, but we can use for N any value smaller than that calculated from Eq. (10). Of course, if we use the maximum value allowed to N, we will get a better result. In the present case we will adopt N=10, for which Eq. (20) furnishes a good enough approximation of the desired function. In FIG. 1 the intensity of the desired longitudinal function F(z) is compared with that of the localized stationary wave field indicated as FW which corresponds to $\Psi(\rho=0, z, t)$, obtained from Eq. (11) by using N=10.

A good agreement between the desired longitudinal behaviour and the localized stationary wave field approximation FW can be observed. Obviously we can improve the approximation by using bigger values of N.

Figure 2:
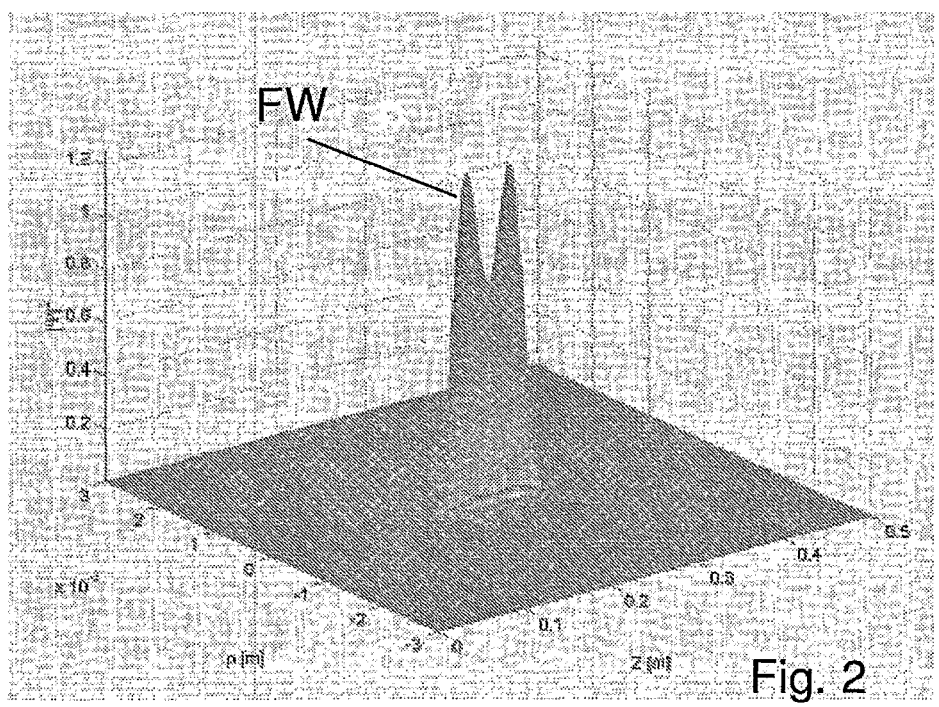
FIG. 2 shows a 3D plot of the field intensity of the localized stationary wave field (FW) chosen by us.
Figure 3:
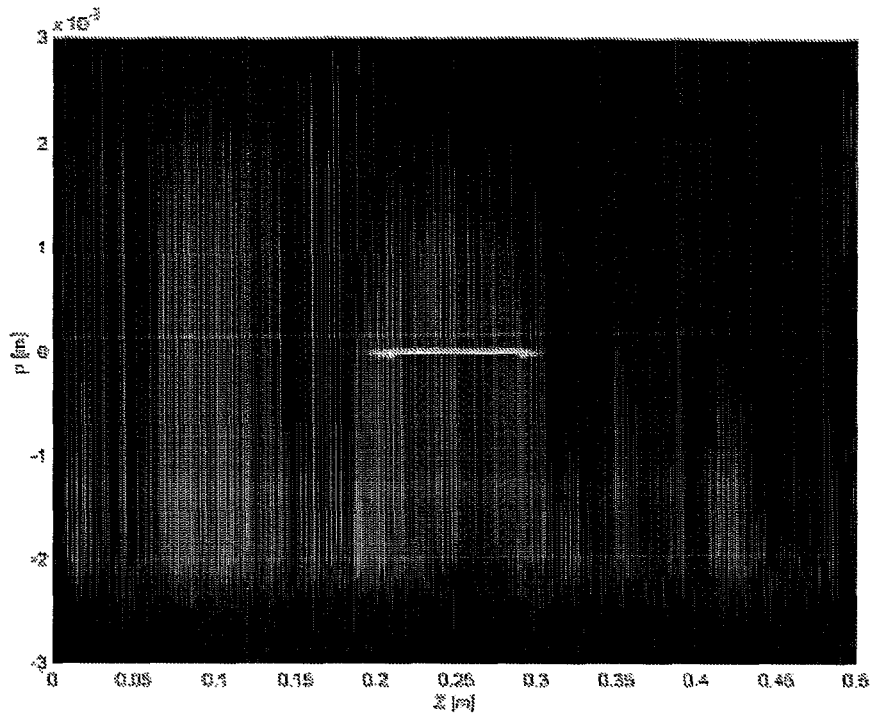
FIG. 3 shows an orthogonal projection of FIG. 2.

In FIG. 2 we show the 3D wave field intensity of the localized stationary wave field FW given by Eq. (13). It appears evident that this field has a good transverse localization and possesses the desired longitudinal pattern. The same figure is shown in FIG. 3, but in an orthogonal projection.

Second Case:

Here, let us suppose that we want an optical wave field with $\lambda=0.632$ μm ($\omega_0=2.98*10^{15}$ Hz), whose longitudinal pattern (on its axis) in the range $0 \leq z \leq 0.5$ m consists in a pair of parabolas, whose centres are located at z=0.22 m and z=0.28 m, with roots at z=0.2 m, z=0.24 m, z=0.26 m and z=0.30 m. Outside the intervals $0.2 \leq z \leq 0.24 \cup 0.26 \leq z \leq 0.30$, we want the function to have zero value. In other words, the desired function is given by:

$$F(z)=-(z-0.20)(z-0.24) \text{ for } 0.20 \leq z \leq 0.24$$

$$F(z)=-(z-0.26)(z-0.30) \text{ for } 0.26 \leq z \leq 0.30 \quad (16)$$

F(z)=0 elsewhere

Again, we can calculate the coefficients $A_n$ by substituting Eq. (16) into Eq. (12), and use them in the superposition given by our Eq. (11). In the present case, we chose $Q=0.9999\ \omega_0/c$: this choice allows a maximum value of n given by N=79 (we can see this from Eq. (9)). But we adopt N=10, for which Eq. (11) already yields a good approximation of the desired function.

Figure 4:
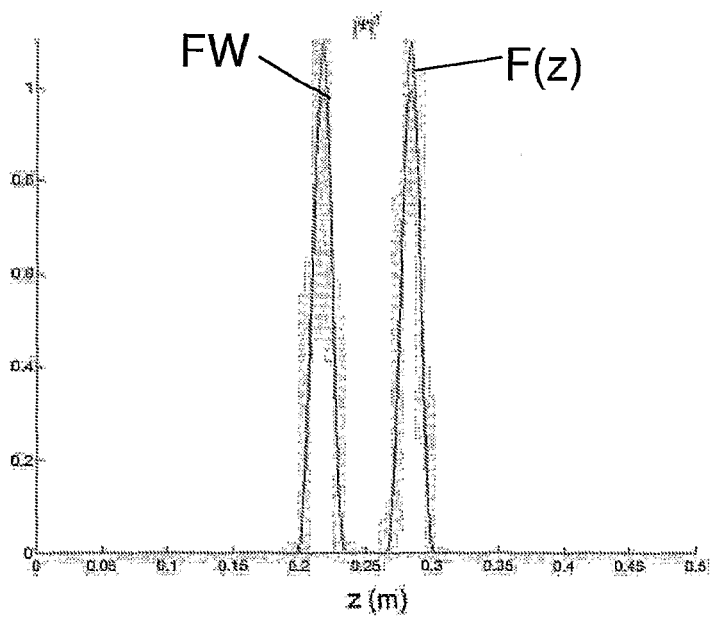
FIG. 4 shows a comparison between the intensity of the desired longitudinal function F(z), given by Eq. (16), and that of the localized stationary wave field, $\Psi(\rho=0, z, t)$, obtained from Eq. (11

FIG. 4 shows the comparison of the intensity of the desired longitudinal function F(z) with that of the localized stationary wave filed approximation FW, $\Psi(\rho=0, z, t)$, obtained from Eq. (11) with N=10: A good agreement between the desired longitudinal behaviour and the localized stationary wave field FW can be observed. Obviously we can improve the approximation by using higher values of N.

Figure 5:
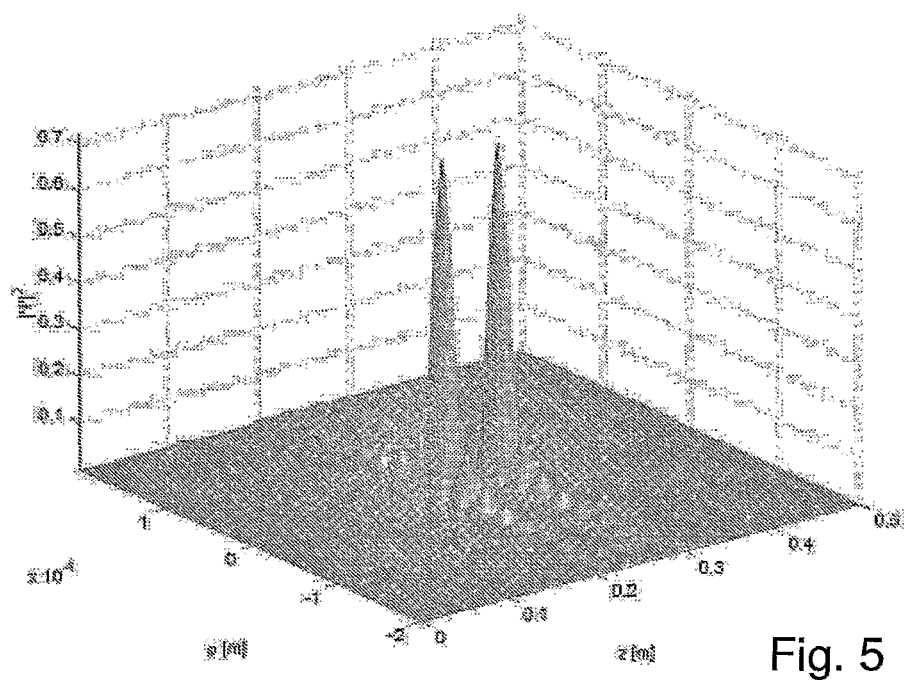
FIG. 5 shows a 3D plot of the field intensity of the localized stationary wave field considered by us.
Figure 6:
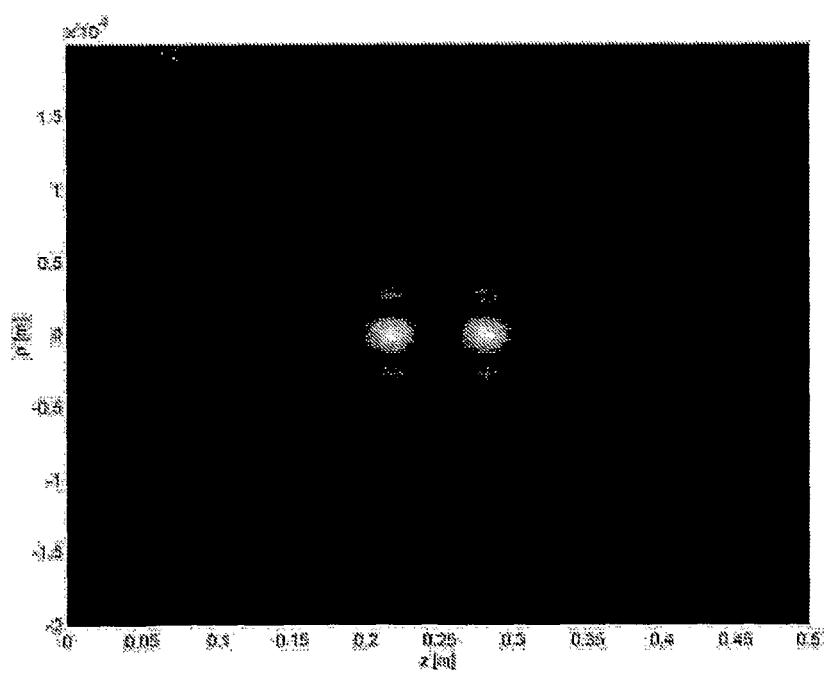
FIG. 6 shows an orthogonal projection of FIG. 5.

FIG. 5 shows the 3D wave field intensity of the localized stationary wave field approximation FW given by Eq. (13). We can see that this field has a good transverse localization and possesses the desired longitudinal pattern. The same figure is shown in FIG. 6, but in an orthogonal projection.

The Source for Generating Localized Stationary Wave Fields According to the Invention In accordance with the previous method for generating localized stationary wave fields, it is possible to construct solutions of the wave equation with the desired stationary longitudinal pattern on their axis within the range $0 \leq z \leq L$, and with a high transverse field concentration, just by making a suitable superposition of Bessel beams. In the particular embodiment of the method described herein the superposed Bessel beams are Bessel beams having the same frequency. In this way, if any experimental apparatus capable of generating a Bessel beam is available, an array of such apparatuses can be used to generate a sum of Bessel beams with the appropriate (longitudinal) wavenumbers, amplitudes and phases, and by this array we can generate the stationary wave fields according to the invention.

It has to be noticed that the Bessel beams of the superposition can also be non monochromatic. For example the Bessel beams may be pulses having a certain bandwidth or the Bessel beams may also have different frequencies.

A first example of a source of a single Bessel beam can be constructed by using the very simple experimental apparatus of Durnin et al. Such source is illustrated in FIG. 7.

Figure 7:
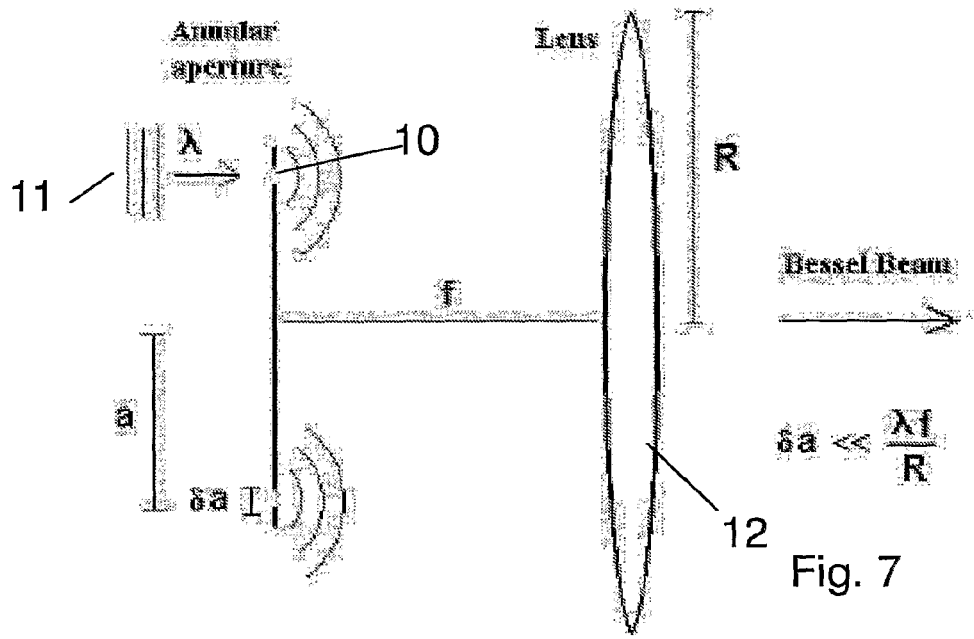
FIG. 7 illustrates schematically the experimental apparatus adopted by Durnin et al. as a possible set-up for generating a Bessel beam.

Referring to FIG. 7, as is well-known since the experiment by Durnin et al. in 1987, a very simple way to generate a Bessel beam is using an annular slit 10 located in the front focal plane of a convergent lens 11 and illuminated by a cw laser 12.

Let a be the radius of the annular slit, μa its thickness, λ the wavelength of the laser, and f and R focal length and radius of the lens, respectively. On illuminating the annular slit with a cw laser of frequency $\omega_0$, and provided that the condition $\delta\alpha \ll \lambda f/R$ is satisfied, the Durnin et al.'s apparatus generates, after the lens, a wave field similar to a Bessel beam along a certain field depth, i.e., within a certain range of distance. Within this range, given by $0 \leq z \leq Z \approx R\ f/\alpha$, the generated Bessel beam can be written as:

$$\psi(\rho,z,t)=\Lambda J_0(k_\rho \rho)e^{i\beta z}e^{i\omega_0 t} \quad (17)$$

with $\Lambda$ constant depending on the values of $\alpha$, f, $\omega_0$ and $$k_\rho = \frac{\omega_0}{c} \frac{a}{f} \quad (18)$$

and $$\beta^2 = \frac{\omega_0^2}{c^2} - k_\rho^2 \quad (19)$$

Thus we can see that the transverse and longitudinal wavenumbers are determined by radius and focus of the slit and lens, respectively. Once more, we recall that the wave field will approximately possess a Bessel beam behaviour in the range $0 \leq z \leq Z \approx R\ f/\alpha$, which we have called field depth of the Bessel beam in question.

Figure 8:
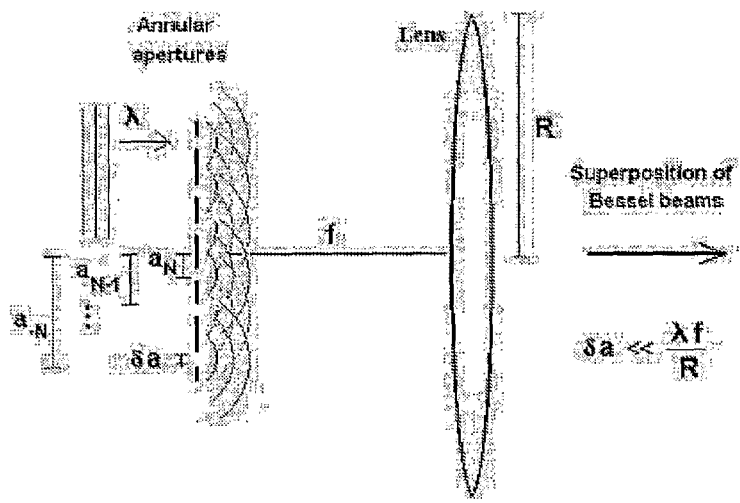
FIG. 8 illustrates a suitable, concentric annular slits array for generating a particular superposition of Bessel beams, and in particular a localized stationary wave field (FW) according to the invention.
Figure 9:
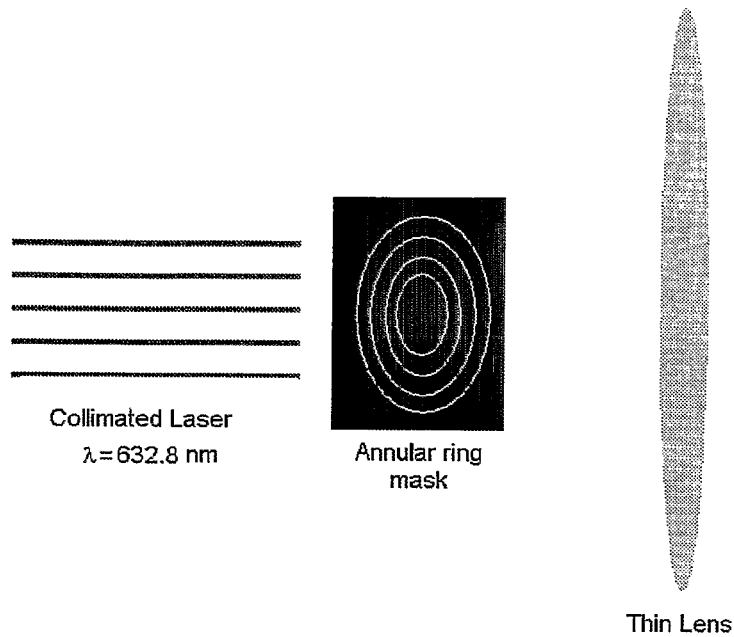
FIG. 9 illustrates schematically the experimental set-up constituted by laser beam, a set of annular apertures, and a thin lens.
Figure 10:
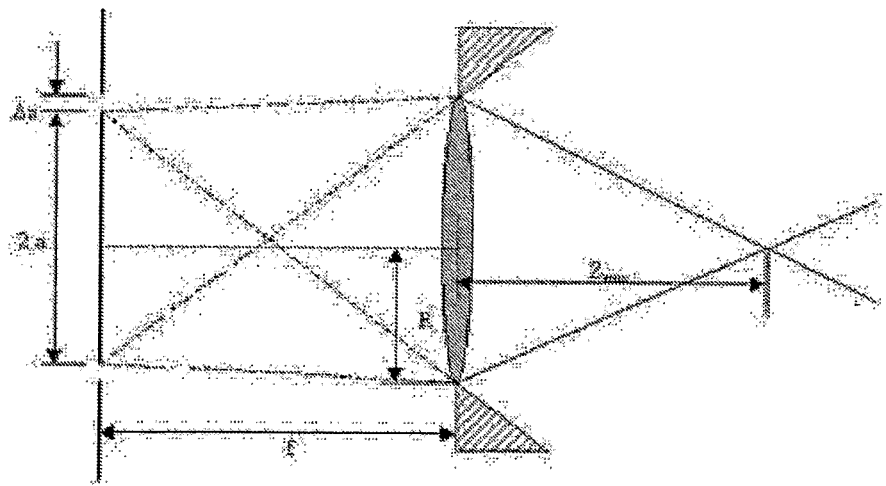
FIG. 10 illustrates a geometrical scheme of the previous experimental set-up in FIG. 9.
Figure 11:
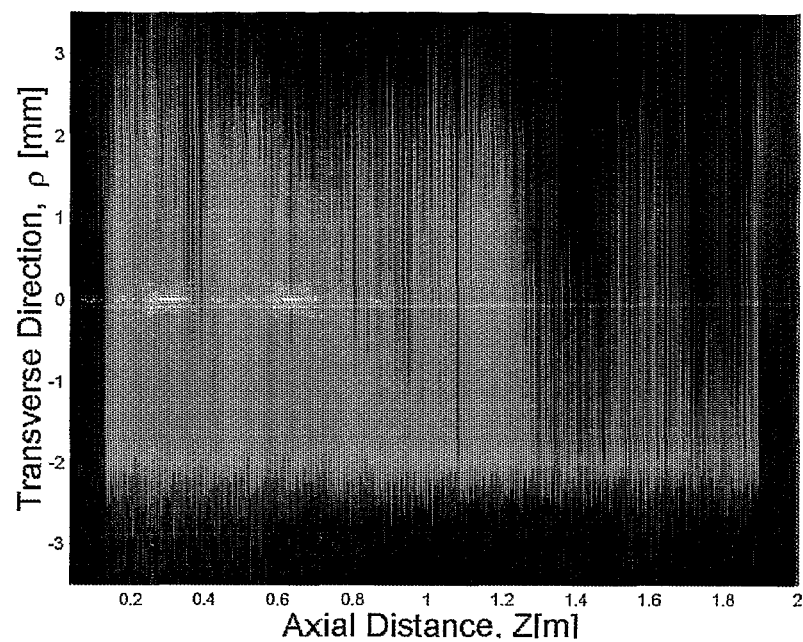
FIG. 11 shows an example of a two-peak stationary wave field corresponding to a calculated set of slit-radius values.
Figure 12:
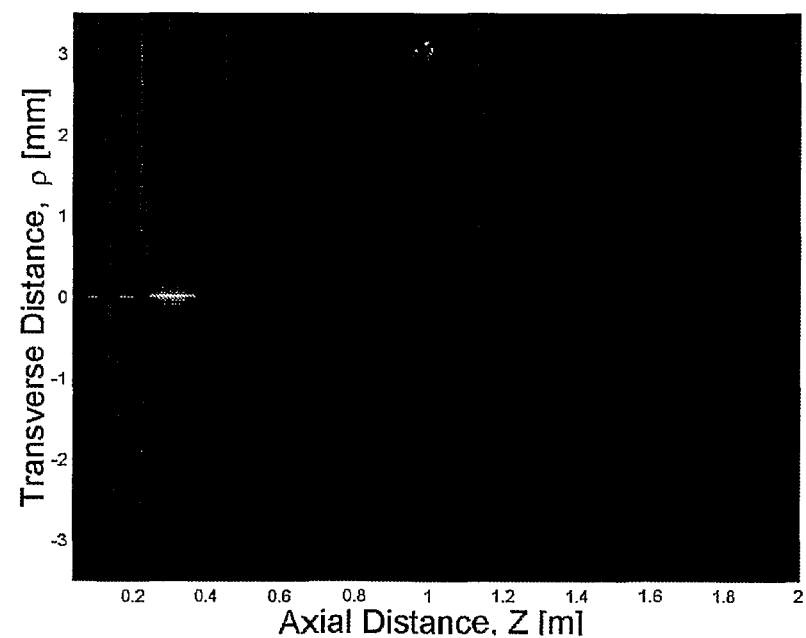
FIG. 12 shows an example of a single-peak stationary wave field corresponding to another calculated set of slit-radius values.

As we have seen from the previous Sections, the localized stationary wave fields according to the invention are obtained by suitable superpositions of Bessel beams. So we can construct experimentally the localized stationary wave fields for instance by using several concentric annular slits as illustrated in FIG. 8, where each radius is chosen to yield the correct longitudinal wavenumber, and where the transfer function of each annular slit is chosen in order to correspond to the coefficients $A_n$ of Eq. (11), which are necessary for obtaining the desired longitudinal pattern.

To explain the above matter in greater detail, let us suppose that we have 2N+1 concentric annular slits with radii $a_n$, with $-N \leq n \leq N$. Along a certain range after the lens, we'll have a wave field given by the sum of the Bessel beams produced by each slit:

$$\Psi(\rho, z, t) = e^{-i\omega_0 t} \sum_{n=-N}^{N} \Lambda_n T_n J_0(k_{\rho n}\rho)e^{i\beta_n a} \quad (20)$$

where $T_n$ are the possible transfer functions of each annular slit (regulating amplitude and phase of the emitted Bessel beams, and regarded as constants for each slit), while $\Lambda_n$ are constants depending on the characteristics of the apparatus which can be approximately written as $$\Lambda_n = \frac{a_n \omega_0 \exp\left[\frac{i\omega_0 a_n^2}{2cf}\right]}{2\pi cfi} \quad (21)$$

which is valid when $\alpha_a$ is very small. The transfer functions can be determined experimentally or empirically. In optics for example by covering the annular slits by a superthin film or in acoustic by correspondingly exciting the transducers. An alternative way is to use additional lenses as it will be explained better in the following Moreover, the transverse and longitudinal wavenumbers are given by $$k_{\rho n} = \frac{\omega_0}{c} \frac{a_n}{f} \quad (22)$$

and $$\beta_n^2 = \frac{\omega_0^2}{c^2} - k_\rho^2 \quad (23)$$

On the other hand, we know from our method that for constructing the localized, stationary wave fields we must have β given by Eq. (9):

$$\beta_n = Q + \frac{2\pi}{L} n$$

On combining together Eqs. (9, 22, 23), we get $$\left(Q + \frac{2\pi}{L}n\right)^2 = \frac{\omega_0^2}{c^2} - \left(\frac{\omega_0^2}{c^2} \frac{a_n}{f}\right)^2 \quad (24)$$

and solving with respect to a_n we obtain $$a_n = f\sqrt{1 - \frac{c^2}{\omega_0^2}\left(Q + \frac{2\pi}{L}n\right)^2} \quad (25)$$

Equation (25) yields the radii of the annular slit that provide the correct longitudinal wavenumbers for the generation of the localized, stationary wave fields according to the invention. However, the procedure is not ended.

Once the desired longitudinal pattern F(z) is chosen, in Eq. (13) we necessarily meet the coefficients A_n given by Eq. (12). Such coefficients must be the coefficients of Eq. (20). To obtain this, it is necessary that each annular slit has an appropriate transfer function, which will regulate amplitude and phase of each Bessel beam emitted by the slits. By using Eqs. (11, 12, 20) we obtain that the transfer function T_n of the n-th annular slit has to be:

$$T_n = \frac{A_n}{\Lambda_n} = \frac{1}{L\Lambda_n} \int_0^L F(z) e^{-i\frac{2\pi}{L}nz} dz \quad (26)$$

where $\Lambda_n$ is given by Eq. (21).

Therefore, with the radius of each annular slit given by Eq. (25) and the transfer functions of each slit given by Eq. (26), we can obtain a localized stationary wave field FW that has the desired longitudinal behaviour in the range 0≦z≦L.

Obviously we have to guarantee that the distance L is smaller than the smallest Bessel beam field-depth among the Bessel beams in the superposition (20). In either words, we must have:

$$L \le Z_{min} \approx \frac{Rf}{a_{max}} \quad (27)$$

where a_max is the biggest radius of the concentric annular slits.

In the following two experimental apparatuses are illustrated, which generate different localized stationary wave fields.

I. Experimental Apparatus Producing Two Intensity Peaks

With regard to the annular ring mask, one can consider four concentric annular rings, with the following radii a__1=1.099 mm
a__2=1.253 mm
a__3=1.386 mm
a__4=1.504 mm, all of them having the same thickness, Δa=10 μm (which is actually a limit value: higher values should not be used), and, for simplicity's sake, the same transfer function, equal to unity. In this situation, we chose a CW laser with λ=632.8 nm, and a thin lens with focal distance f=30.5 cm and radius R=3.5 mm. With these parameters, peaks are produced at 31.5 cm and 63 cm:

II. Experimental Apparatus Producing a Single Intensity Peak

With regard to the annular ring mask, one can consider 4 concentric annular rings, with the following radii a__1=2.303 mm
a__2=2.380 mm
a__3=2.451 mm
a__4=2.518 mm, all of them having the same thickness Δa=10 μm. In this situation, we chose a CW laser with λ=632.8 nm, and a thin lens with focal distance f=30.5 cm and radius R=3.5 mm. With these parameters, a peak is produced at 32 cm.

More in general, our method is able to yield a mathematical model, and the characteristics for design and construction of the source by using arrays of sources for Bessel beams.

According to a first embodiment of the said sources, a source for generating a superposition of Bessel beams, which is suitable for generating a localized stationary wave field in one or more confined space-regions, comprises at least one source beam generator: Namely, at least one diffraction pattern against which the entering monochromatic beam is directed, the diffraction pattern being created for instance by an array of coaxial annular slits. Radius and transfer function of each annular slit are related to the longitudinal wavenumber (and therefore with the transverse wavenumber too), to the amplitude, and to the phase of the Bessel beam to be generated by the said annular slit.

Furthermore a lens is provided after the array of coaxial annular slits, so that the array results to be located in the rear focal plane of the lens; the said lens correcting the phase of the waves impinging on it, and contributing to determine, together with the annular radius of each slit, the transverse, and longitudinal, wavenumber of the corresponding Bessel beam.

A single frequency is used. The kind of source beam and of the diffraction device and/or of the lens depends on the desired frequency range and type of waves. Till now the method has not been restricted to any particular kind of wave and thus it can be applied to any kind of waves existing in nature, such as for example: mechanical waves as acoustic waves or the like; electromagnetic waves such as light, or laser beams, or microwaves; or even gravitational waves, or waves describing elementary particles.

Let us explicitly recall that the transfer function of each annular source has to be produced either by suitably exciting the corresponding transducer, or, in the optical case, by covering each annular slit by the required super-thin film determining amplitude and phase of the Bessel beam generated by the said slit. Such a set of super-thin films, however, can be replaced by a set of supplementary lenses: Essentially, by a second lens, identical with the previous one, but justaposed to the diffracting array. Due to the action of the lens located immediately after the slit array, the transfer function $T_n$ of each slit becomes a real quantity equal to $A_n$, at variance with the relation $T_n = A-N/\alpha_n$, given by Eq. (26).

More specifically, the Transfer Functions of the annular slits provides the corresponding Bessel beam with the correct amplitude and phase. The transfer function $T_n$ of the n-th annular slit must be given by Eq. (26), where $\alpha_n$ is the complex weight of the Bessel beam generated by the n-th slit when its transfer function is equal to 1. When $\alpha a$ is almost equal to zero, the value of $\alpha_n$ is given by Eq. (21). As already said, the transfer function $T_n$ can be obtained by putting thin films on the surface of the n-th slit. The action of a thin-film is as follows: Let us consider an wave coming from a $1^{st}$ medium, with refraction index $n_1$, meeting (e.g., orthogonally) a film with width d and refraction index $n_2$ (which can be complex, due to absorption, $n_2 = N\_2 + i$ alpha), and going on to a $3^{rd}$ medium with refraction index $n\_3$. Meeting the film, the incoming wave is partially reflected and partially refracted (i.e., transmitted into the film). Inside the film multiple reflections take place, while each reflected wave in its turn is partially refracted and transmitted into the $3^{rd}$ medium (and also into medium $1^{st}$, but this is of no interest for us). The total wave reaching the $3^{rd}$ medium is the sum of the all the previous transmitted waves, and its amplitude and phase will depend on $n_1$, $n_2 = N\_2 + i$ alfa, $n_3$, and d. In our case (air-film-air) $n_3 = n_1$, and we can choose $N\_2$, alpha, and d in order to get the desired amplitude and phase of the wave coming out from the film. One can even use a set of superposed thin-films, to increase the degrees of freedom, tunable so to obtain the desired effect. The transfer functions T_n can be generated in such a way. Going back to the invention, os coefficients $A_n$ according to the method must be os coefficients of the Bessel beams generated by the apparatus considered in the invention. In the typical case of annular slits, if we do not cover them with a film, each slit generates a Bessel beam with a coefficient that has been called $\alpha_n$ above in this patent. When we have, by contrast, a transfer function $T_n$ for each slit (differing from slit to slit, but constant for each slit), the coefficient of the Bessel beam generated by the said slit becomes $T_n \alpha_n$: But we want such a coefficient to be $A_n$; therefore, according to the method here disclosed it must be $T_n = A_n/\alpha_n$. All such a procedure can be however facilitated by adding an extra lens (with focal distance equal to that of the other lens) immediately after the plane of the slits: In this way as already mentioned the transfer functions $T_n$ are made equal to $\alpha_n$ (that is, $T_n = \alpha_n$), where $\alpha_n$ are the coefficients of our superposition given by Eq. (12), and can be rendered real numbers by suitable choices of $F(z)$ and the interval $0 \leq z \leq L$.

With regard to the behavior of the localized stationary wave field in media without losses, the theory of the stationary wave fields according to the present invention can furnish results similar to the free-space ones. This happens because the stationary wave fields according to the invention can be built up via suitable superposition of Bessel beams of the same frequency, so that there is no problem with the material dispersion.

However, in LOSSY MEDIA, some care is in order. Surprisingly, for Bessel beams the absorption coefficient in the direction of propagation depends on the longitudinal wavenumber, besides on the frequency. Consequently, each Bessel beam in the mentioned superposition will have a different attenuation in the longitudinal direction: This affects the structure of the localized stationary wave fields defined according to the above mentioned method, and some technical tricks can be accordingly used, as explained in the following.

An appropriate choice of the parameters can overcome the mentioned problem. We shall describe the behavior of the method at first in lossless media, mentioning afterwards lossy media.

Localized Stationary Wave Fields in Lossless Media

On using the above mentioned method and theory of the localized stationary wave fields, we can construct (as an example) a field with the desired longitudinal pattern inside a certain spatial interval: for instance, $0 \leq z \leq \_L$; so that it results spatially concentrated in the surrounding of a specific point. The residual intensity of this field will depend on the number of Bessel beams used to construct the localized stationary wave field. Namely, on the number of terms of the Fourier series that will suffice for approximating the desired longitudinal intensity pattern.

Some field configurations require for example many Bessel beams in the superposition: It is the case in which the width of the localized stationary wave field is much smaller than its distance from the source. The number of Bessel beams in the superposition is limited (according to the disclosed method) by the parameters Q, L, and by the experimental apparatus itself (besides the chosen frequency).

The original theory of the localized stationary wave fields (by M. Zamboni-Rached, E. Recami, et al.) supports the disclosed method by many more items than those that can be here exploited or employed.

Given a desired longitudinal pattern, there are many different methods to reproduce it by the theory. The choice of the best method depends on the limitations of the available apparatus, on the field nature or conditions, etc.

Localized Stationary Wave Fields in Lossy Media

In a lossy medium, each Bessel beam of the superposition furnished by the method will suffer a different attenuation coefficient $\alpha_n$ (corresponding to the Bessel beam with longitudinal wavenumber $\alpha_n$). When multiplying each Bessel beam of the said superposition by its loss-factor $\exp[-\alpha_n z]$, the superpositions is no longer a Fourier series, since the factors $\alpha_n$ are different. This is not a problem. Indeed, when using longitudinal coefficients approximately equal one to the other (as it is the case, in general), then the attenuation coefficients $\alpha_n$ will be almost equal, so to be all replaceable by their average value $\alpha = (\alpha_1 + \alpha_2 + \ldots + \alpha_N)/N$. Then, all terms of the trigonometric series (defining the FW according to the method) result to be multiplied by the same, common factor $\exp[-\alpha z]$, which can be taken out of the series: So that, according to the invention, one still get a Fourier series multiplied by the said constant factor; namely, $\alpha(\alpha,z,t) = \exp[-\alpha z] * \exp[iQz - i\alpha_0 t] * \text{Series}$, when * indicates ordinary multiplication, and Series is the ordinary Fourier-Bessel series furnished by the disclosed method. In conclusion, one can proceed according to the method, even if now the FW field will be attenuated over the distance due to the loss-factor $\exp[-\alpha z]$.

In other words, in lossy media with homogeneous characteristics, there will be no problem, except for the attenuation taking place with the distance.

In lossy media without homogeneous characteristics, however, also reflection will took place. If the media is layered in the sense of transmission with a symmetry plane for the interfaces, thus resulting in symmetry existing in refraction indexes, the method could again be applied.

If there is no evidence of any symmetry in refraction properties, it will be necessary to introduce the refraction index at any significant point through the media and numerically calculate according to the disclosed method the resulting final field.

As seen above, in homogeneous lossy media an energy reduction took place, the loss having an expression of the type $e^{-\alpha z}$. In this case—when the loss is of a limited amount, of the order e.g. of 10-20% of the total initial energy—a compensation coefficient of the type $e^{+\alpha z}$ could be added in the superimposition, and the disclosed method could be applied accordingly in order to get again a stationary wave field similar to the one obtained in the case of lossless media according to the invention.

If the loss is greater than 50%, the Frozen Wave can be expected to vanish, as for a plane wave. In any case, the relation to express the loss behaviour can be simplified in the form $I_L = I \exp[-\alpha z\_f]$, where I is the FW peak intensity in the vacuum, I_L is the peak intensity in the lossy medium, and zf is the FW peak position in vacuum for the same situation.

In analogy to the monochromatic wave propagation as used in the disclosed method, the phase velocity is changed but the phase will be unchanged, thus allowing a simple realization of the transducer even for these lossy conditions.

A further parameter influencing the modification in lossy media, is, however, the lossy media longitudinal extension L'. The FW peak according to the disclosed method could not be created, if the wave penetration is less than the distance between the emitter and the desired peak In the following, a method and a technical solution based on the disclosed approach for some particular specific apparatuses and experimental setups are disclosed.

Optics and Microwaves

Optical Case: Situation (1)

Figure 13:
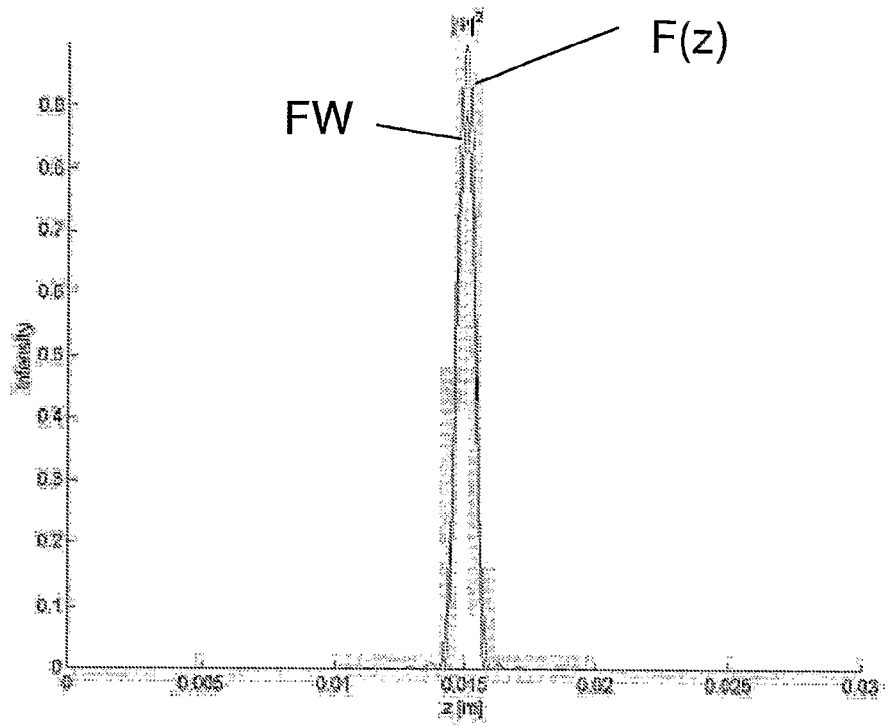
FIG. 13 shows the longitudinal pattern of the localized stationary wave field obtained, according to the invention, from a superposition of 37 Bessel beams, corresponding to situation (1) i.e., to the optical case.
Figure 14:
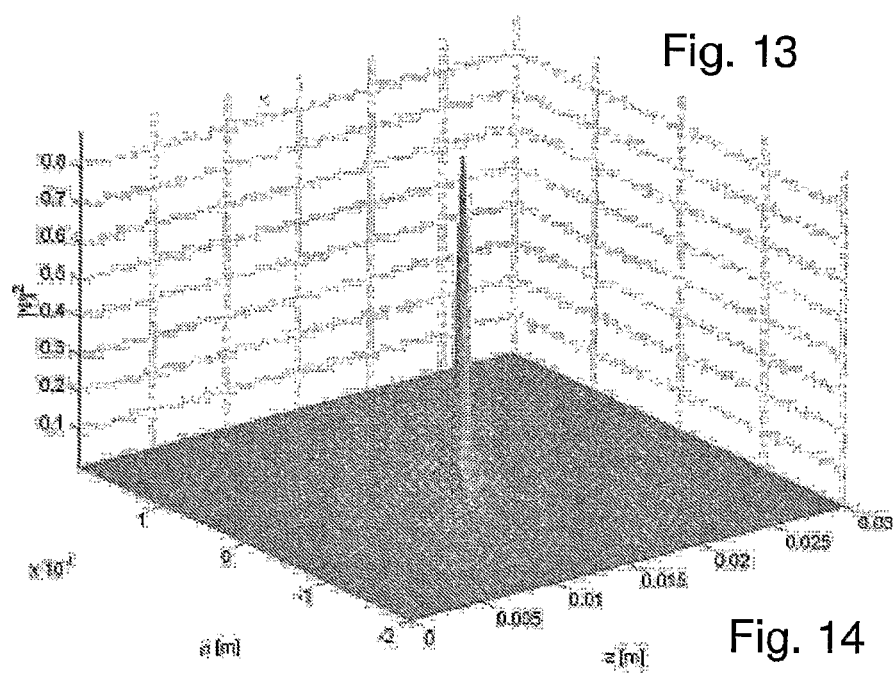
FIG. 14 shows a schematic 3D image of the localized stationary wave field, obtained by superposition of 37 Bessel beams, corresponding to the optical case (situation 1 in the following).
Figure 15:
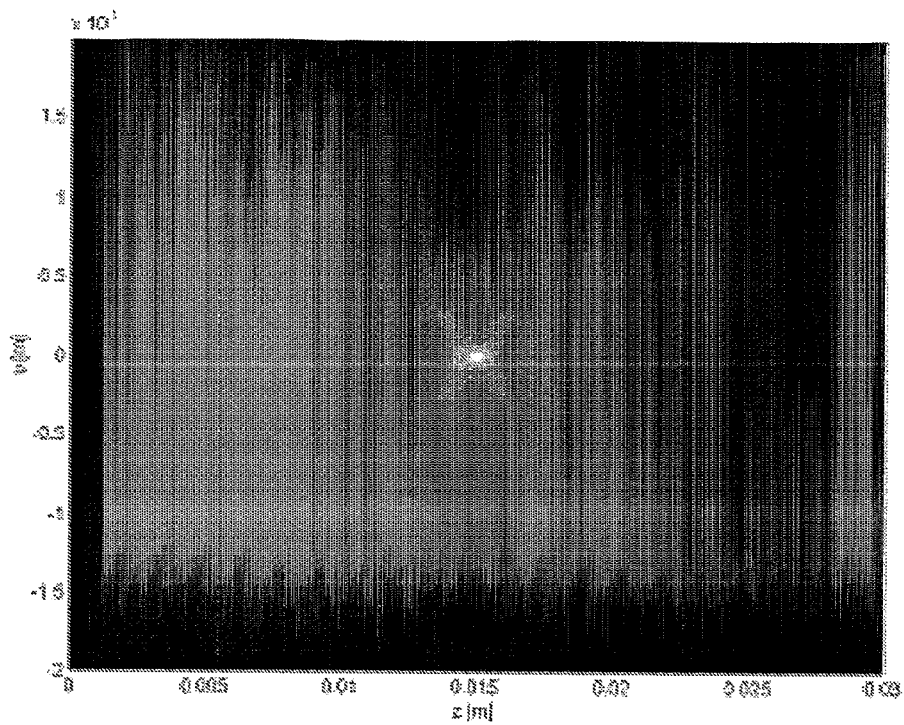
FIG. 15 is an orthogonal projection of FIG. 13
Figure 16:
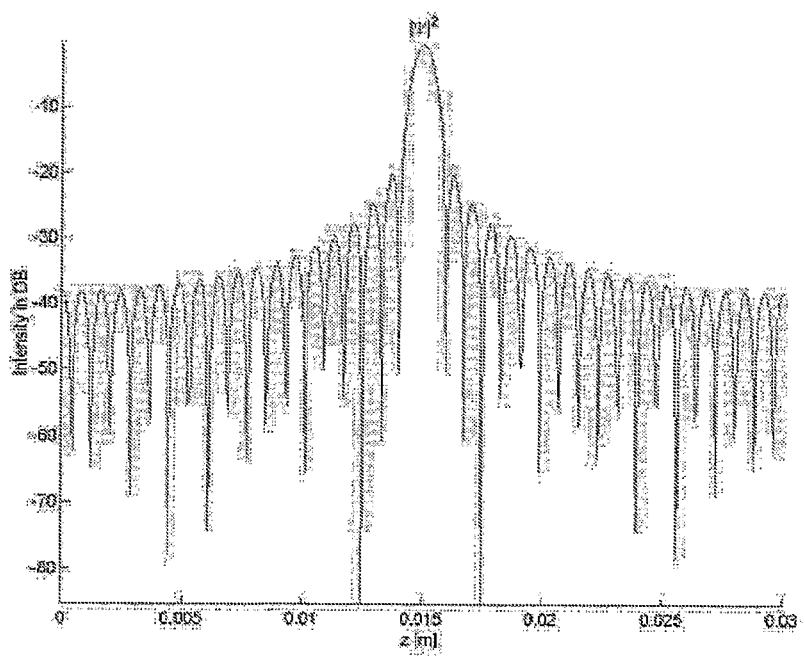
FIG. 16 depicts the same view of FIG. 12 in DB units.
Figure 17:
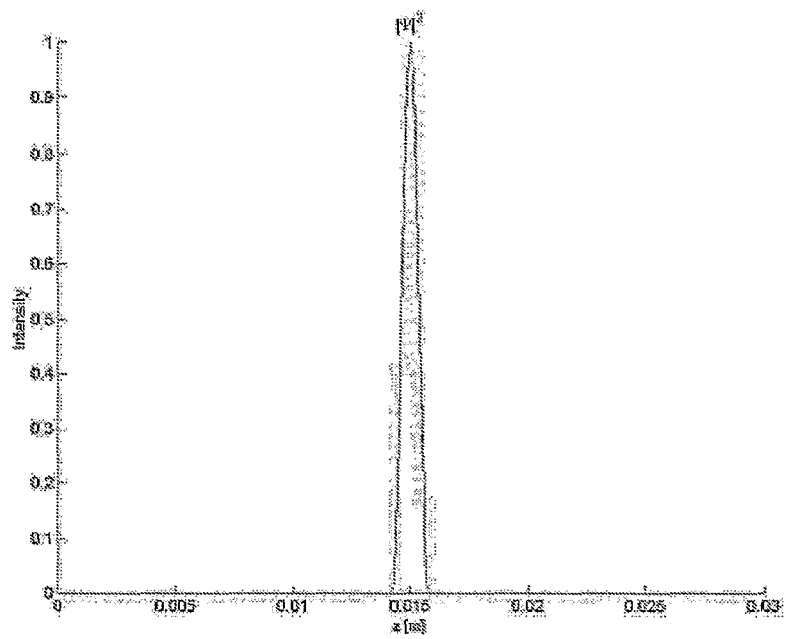
FIG. 17 shows the longitudinal pattern of the localized stationary wave field obtained, according to the invention, by superposition of 181 Bessel beams, corresponding to the optical case.
Figure 18:
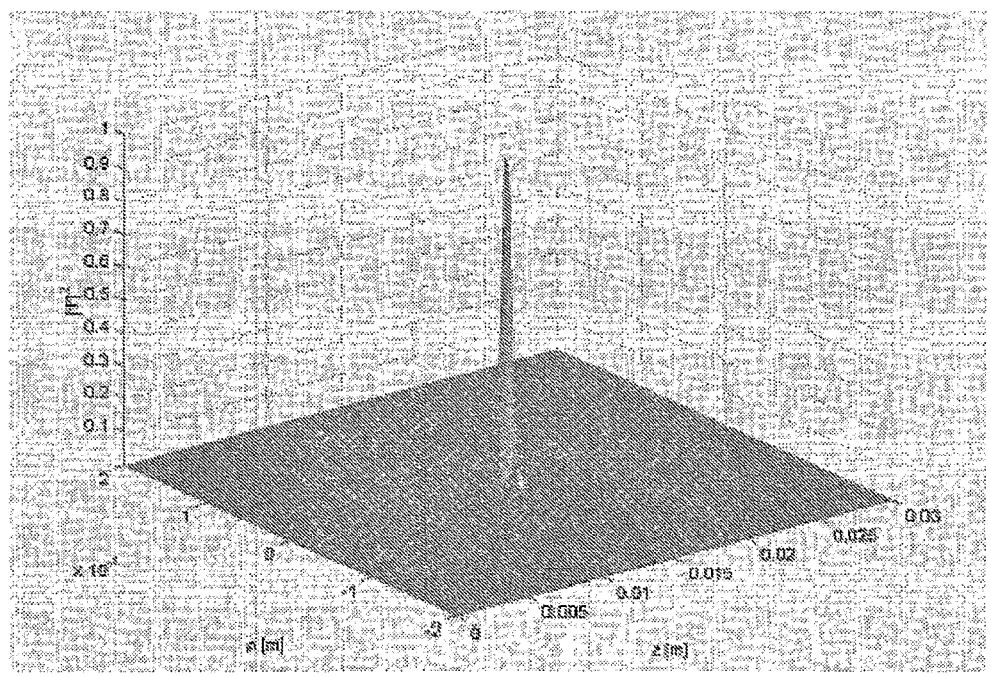
FIG. 18 is a 3D view of the localized stationary wave field represented in FIG. 17, obtained according to the invention by superposition of 181 Bessel beams, and corresponding to the optical case.
Figure 19:
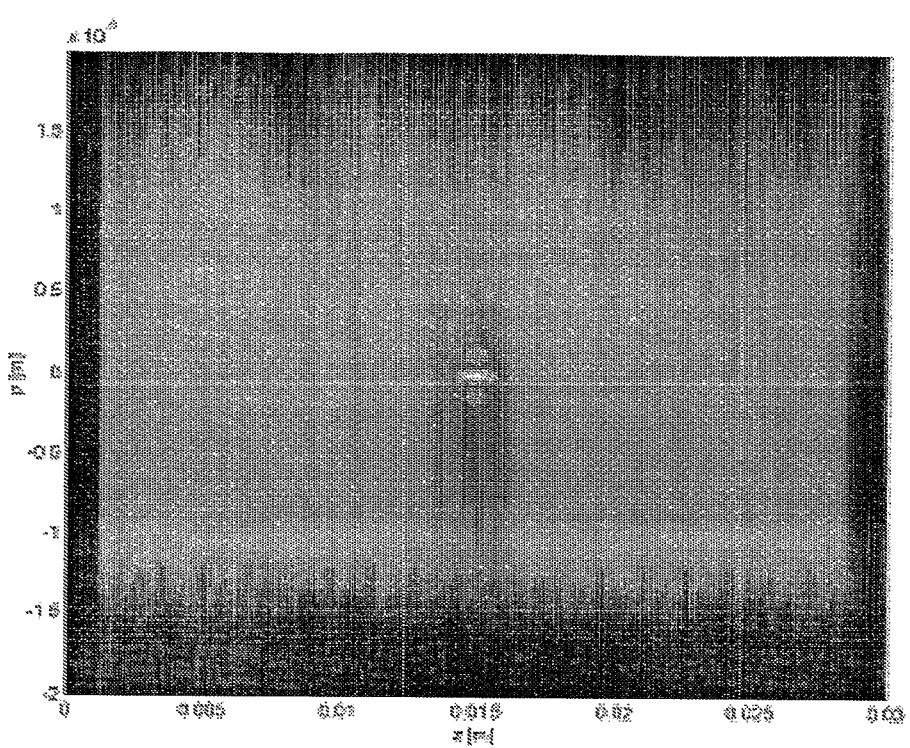
FIG. 19 is an orthogonal projection of FIG. 18.
Figure 20:
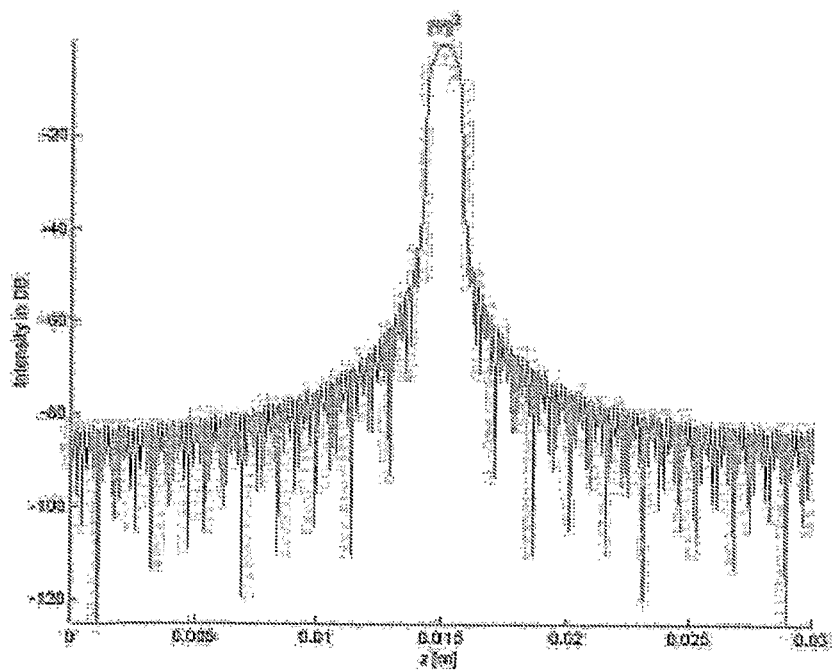
FIG. 20 shows the content of FIG. 18 in DB units.

Let us suppose that it is desired a (free space) optical field ($\mu=0.632$ µm) in the interval $0 \leq z \leq 3$ cm, with a spatial resolution of 1 mm, localized around $z=z_f=1.5$ cm. We can construct this field by using a parabolic function centered at $z_f$ with width of 1.5 mm. See FIGS. 13, 14, 15 and 16 corresponding to this pattern. FIG. 13 shows the 2D plot [line F(z) is the desired field, while line FW is the actually obtained localized stationary wave field]. FIG. 14 is the 3D representation of FIG. 13, and FIG. 15 its orthogonal projection. In FIG. 16 we recast FIG. 13 in decibel, to show the residual intensity in a more clear form.

In this case the source can be manufactured by using an array of annular slits. For the considered localized stationary wave field, the radii of such annular slits must have values of a few millimeters; we need moreover a lens with focal length of 10.5 cm and an aperture of 1.5 mm (source size). For instance, we can use 37 annular slits, with a minimum radius of 0.08 mm (even zero, if one wants) and a maximum radius of 4 mm. Other configurations would be however possible: the proposed configuration is based on an easily available apparatus for fabrication and economical considerations.

Figure 21:
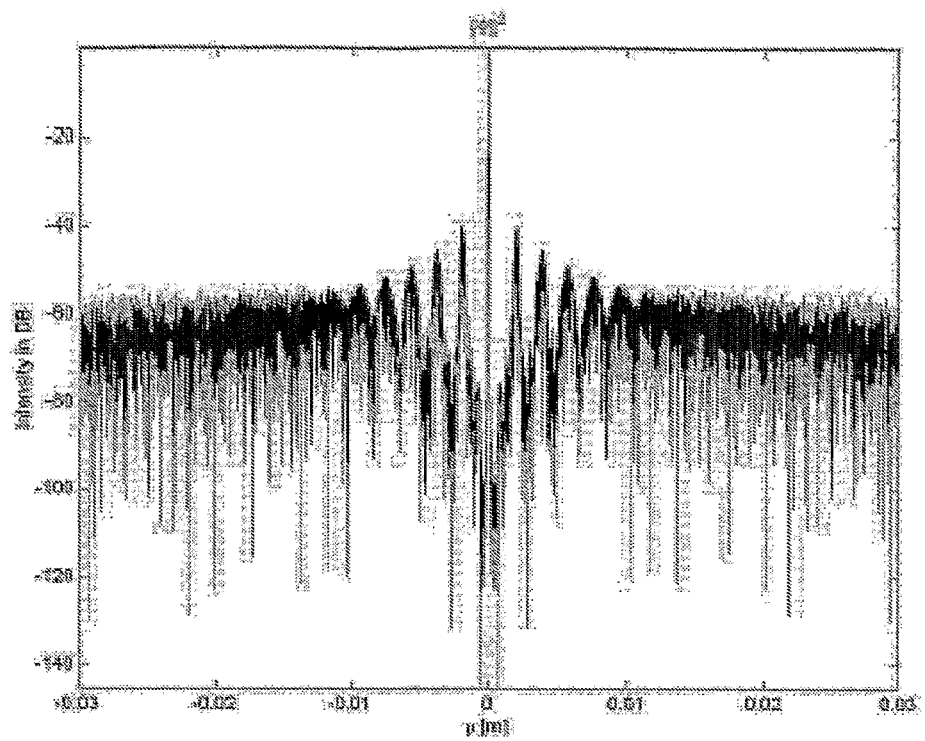
FIG. 21 illustrates the transverse behavior of one of the stationary wave field (obtained according to the invention) in the plane z=zf.
Figure 22:
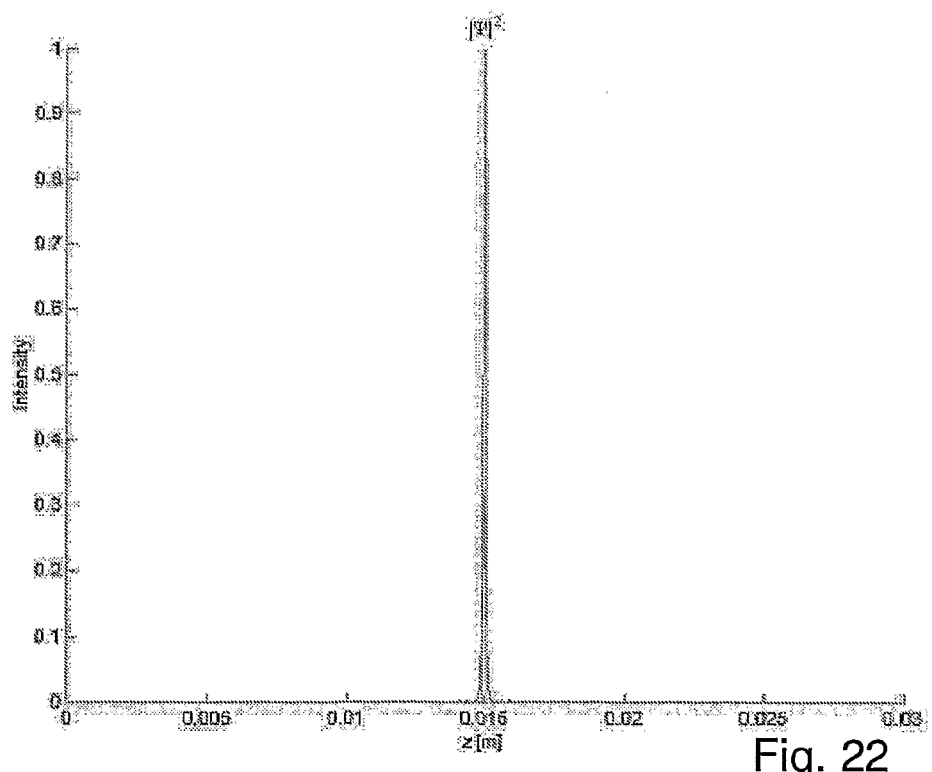
FIG. 22 shows the longitudinal pattern of the localized stationary wave field obtained, according to the invention, by superposition of 181 Bessel beams, corresponding to situation (2) which refers still to an optical case but with an increased spatial resolution of the localized stationary wave field.
Figure 23:
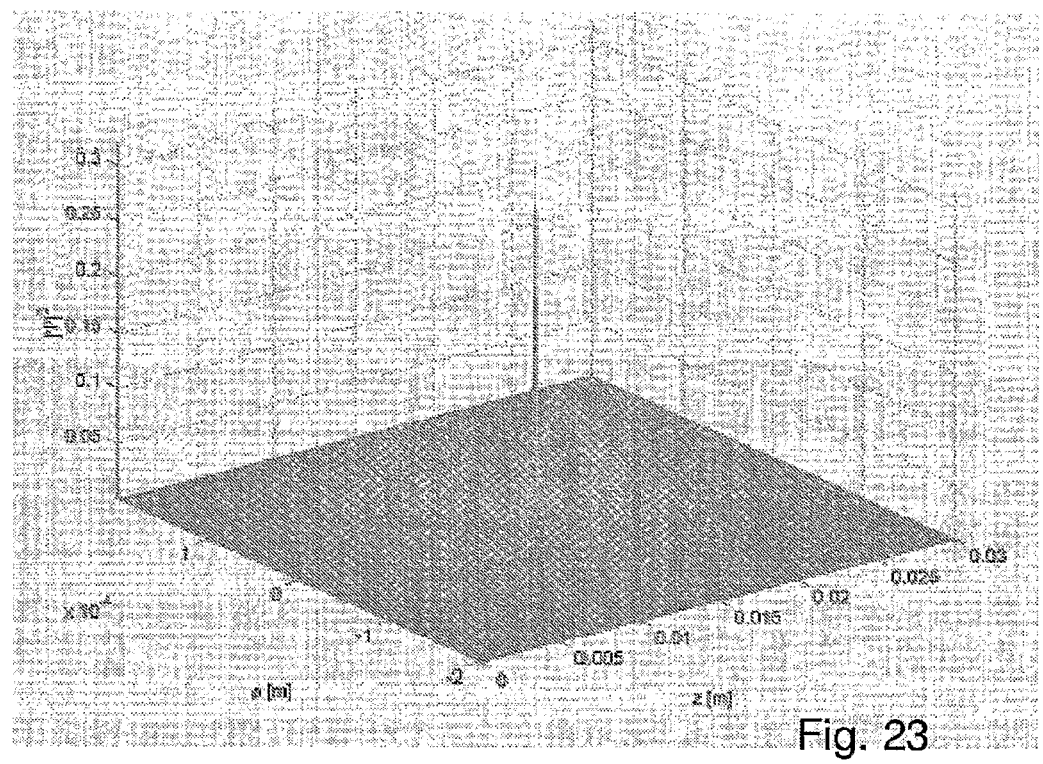
FIG. 23 is a 3D view of the localized stationary wave field represented in FIG. 22, obtained according to the invention by superposition of 181 Bessel beams, and corresponding to situation (2)
Figure 24:
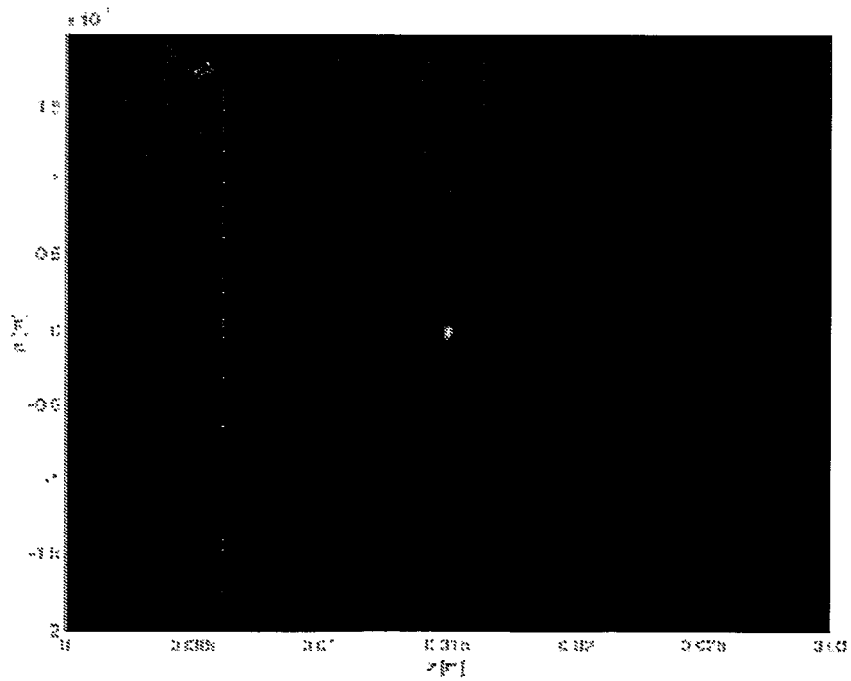
FIG. 24 is an orthogonal projection of FIG. 22
Figure 25:
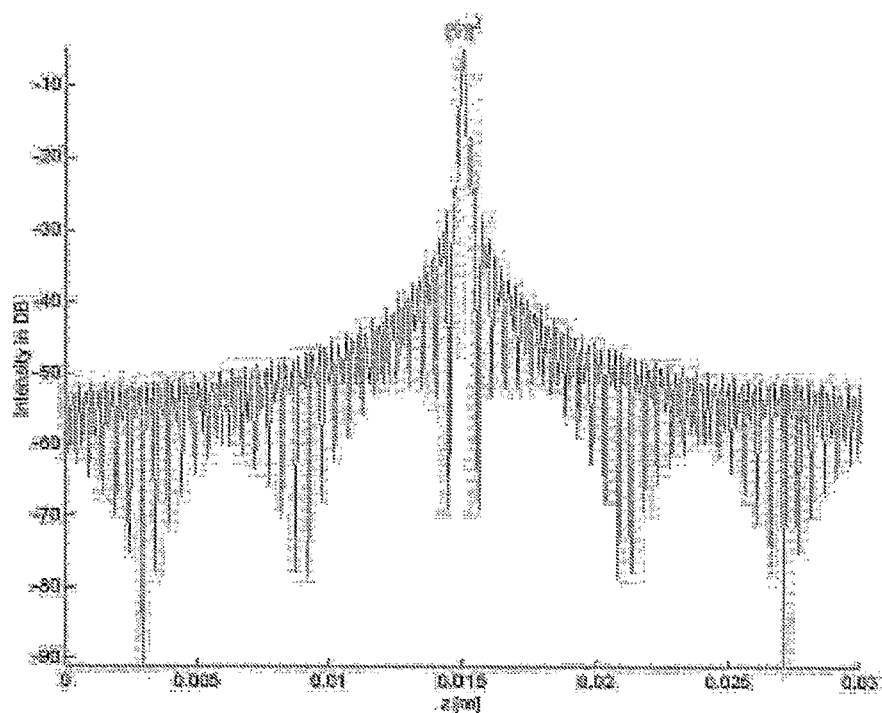
FIG. 25 illustrates FIG. 22 in DB units.
Figure 26:
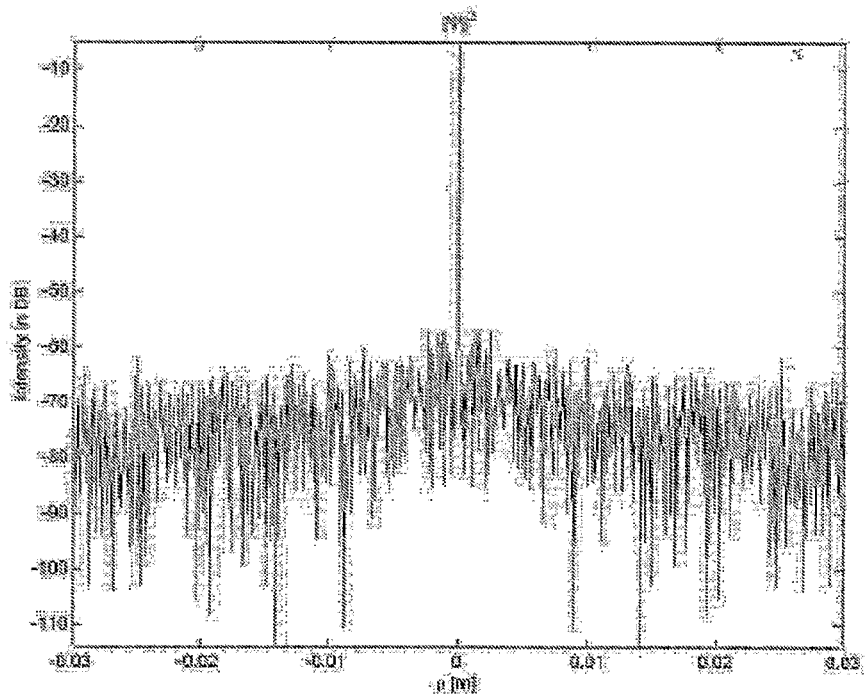
FIG. 26 shows a diagram of the transverse behavior of the localized stationary wave field of FIGS. 22 to 25 in the plane $z=z_f$.

Reducing the Residual Intensity:

The residual intensity of this localized stationary wave field can be reduced. To do this, we need to increase the number of Bessel beams of the generating superposition. Let us suppose that we want the same ideal function as before. The FIGS. 17 to 21 show the improved localized stationary wave field that satisfies this situation: but now we have used 181 annular slits (i.e., 181 Bessel beams) and a lens with focal length of 10.5 cm and aperture of 1.5 mm (new source size). We can observe in FIG. 20 a much smaller residual intensity. In FIG. 21 the transverse behavior of this localized stationary wave field is shown, in the plane $z=z_f$.

Increasing the Spatial Resolution: Situation (2)

The spatial resolution of the localized stationary wave field (FW) can be increased. Let us suppose that we want the same configuration of situation (1), however with a width of 0.15 mm, ten times smaller than before. The FIGS. 22 to 26 show the localized stationary wave field for this situation. We still have 181 annular slits and a lens with focal length of 10.5 cm and aperture of 1.5 mm (source size).

Microwave Case: Situation (3)

Figure 27:
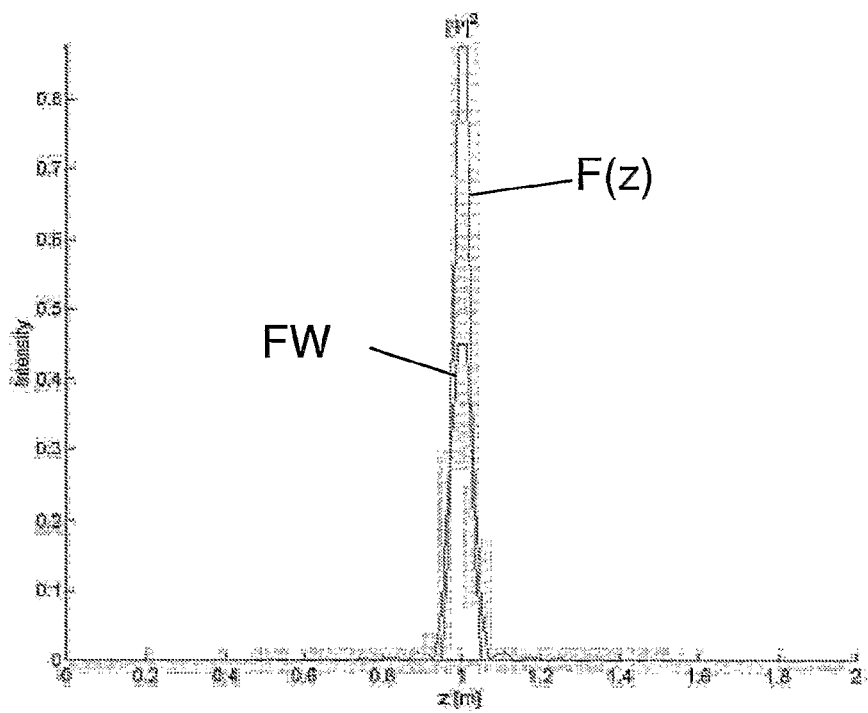
FIG. 27 shows the longitudinal pattern of the localized stationary wave field obtained, according to the invention, by superposition of 29 Bessel beams, and corresponding to situation (3) that is, to the microwave case.
Figure 28:
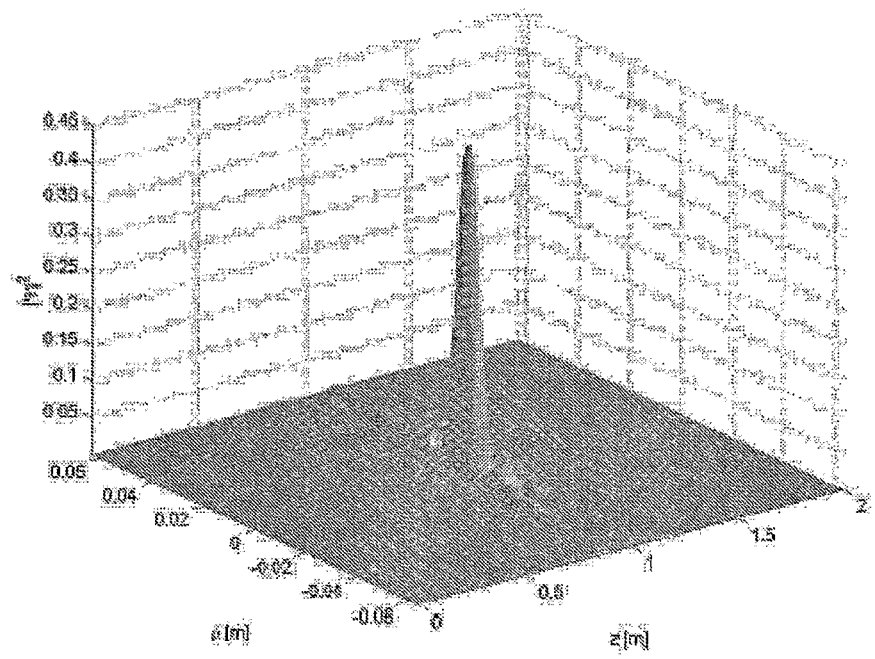
FIG. 28 is a 3D representation of the localized stationary wave field represented in FIG. 27, obtained according to the invention by superposition of 29 Bessel beams, and corresponding to situation (3
Figure 29:
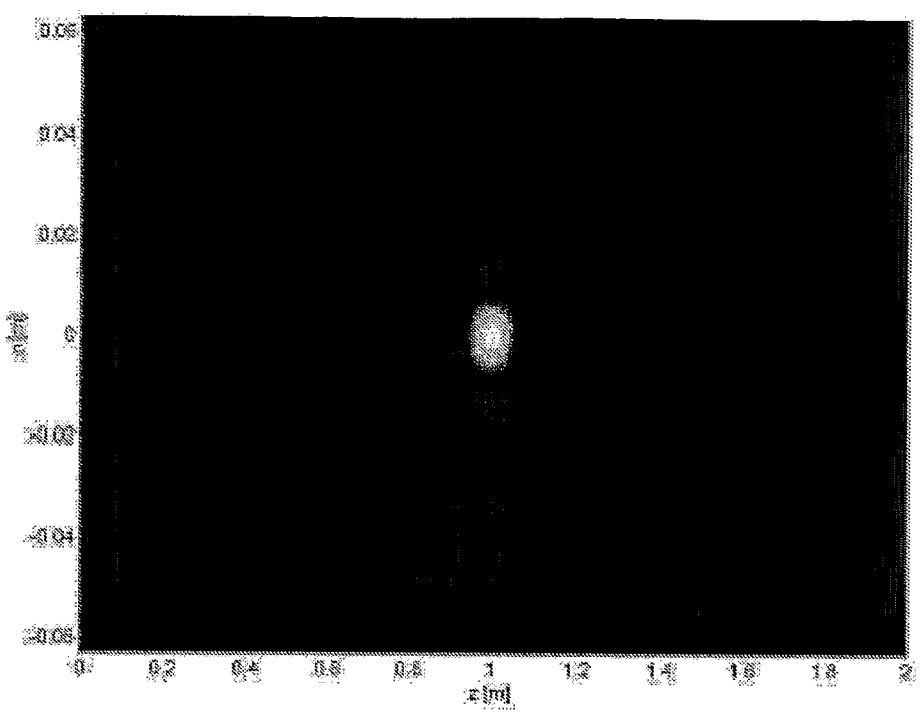
FIG. 29 is an orthogonal projection of FIG. 28
Figure 30:
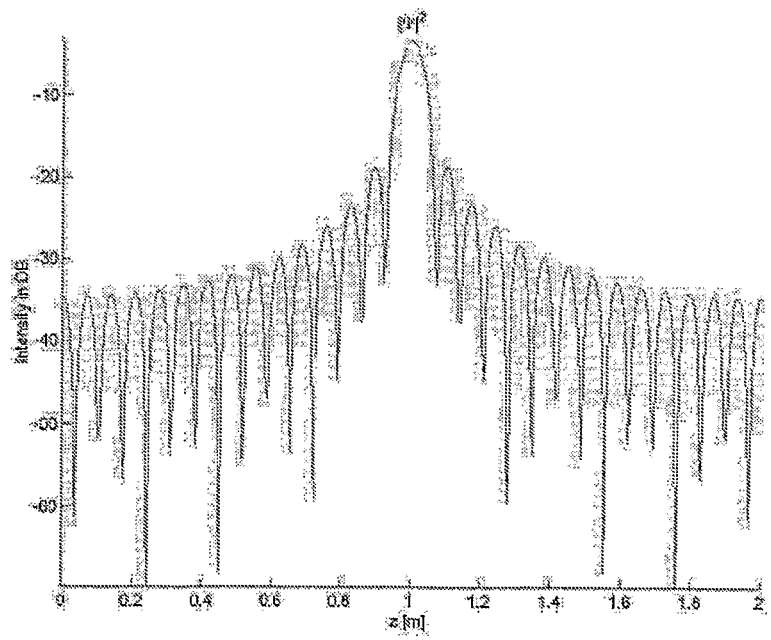
FIG. 30 illustrates FIG. 27 in DB units

Let us suppose that the want a (free space) microwave field ($\mu=1$ cm) in the interval $0 \leq z \leq 2$ m with a spatial resolution of 8 cm, localized around $z=z_f=1$ m. We can construct such a field by using a parabolic function centered at $z_f$ with a width of 8 cm. FIGS. 27 to 30 show such a stationary wave field, by superposition of 29 Bessel beams, corresponding to what we call situation (3). FIG. 27 shows the 2D plot [the line indicated by F(z) is the desired field, while the line indicated by FW is the localized stationary wave field actually obtained] FIG. 28 shows the 3D representation corresponding to FIG. 27, and FIG. 29 is an orthogonal projection. In FIG. 30 we recast FIG. 27 in decibel, to show the residual intensity in a more clear way. In this case the source can be manufactured by using discrete sources located in the plane $z=0$ along a circular aperture of radius 0.7 m, or by using again an array of annular slits. In the latter case, the radii of such annular slits must get values of decimeters, with a microwave lens having a focal length of 1 m and aperture radius of 0.7 m (source size).

We can use 29 annular slits, with a minimum radius of 24 cm and a maximum radius of 56 cm. Other configurations would be possible too.

Acoustics

Acoustic is another field where the localized stationary wave fields FW theory can be applied. In some situations it can be desirable to concentrate a high intensity of acoustic field inside specific regions.

Situation (4)

Now let us suppose that the want an acoustic field with a frequency of 8 MHz in the interval $0 \leq z \leq 20$ cm, with a spatial resolution of 5 mm, localized around $z=z_f=10$ cm. We consider this field created inside a biological tissue, where the sound velocity can be taken as c=1500 m/s, while we are not considering losses. One can construct such pattern by using a parabolic function centered at $z_f$ with a width of 5 mm.

Figure 31:
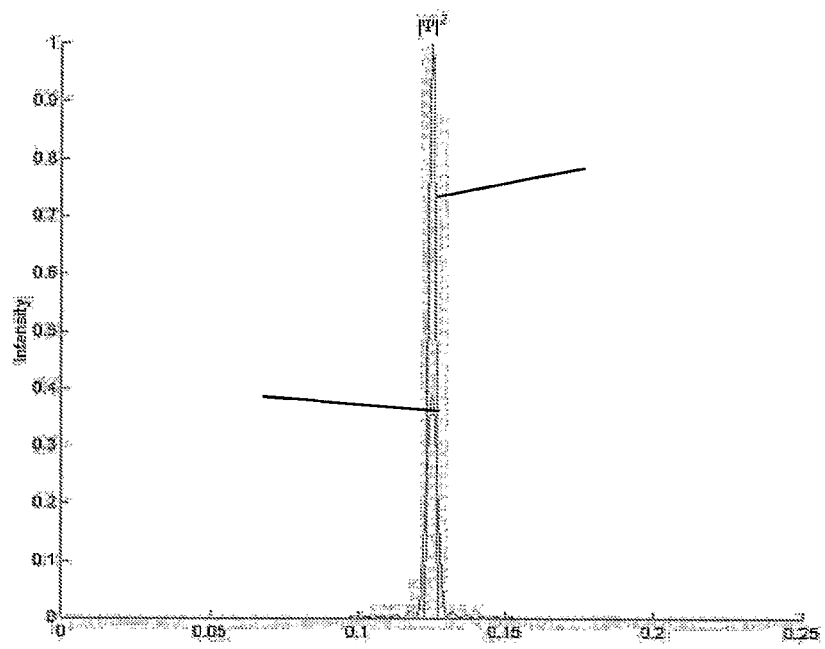
FIG. 31 illustrates the longitudinal pattern of the localized stationary wave field obtained, according to the invention, by superposition of 181 Bessel beams, corresponding to situation (4) that is, to the acoustic case
Figure 32:
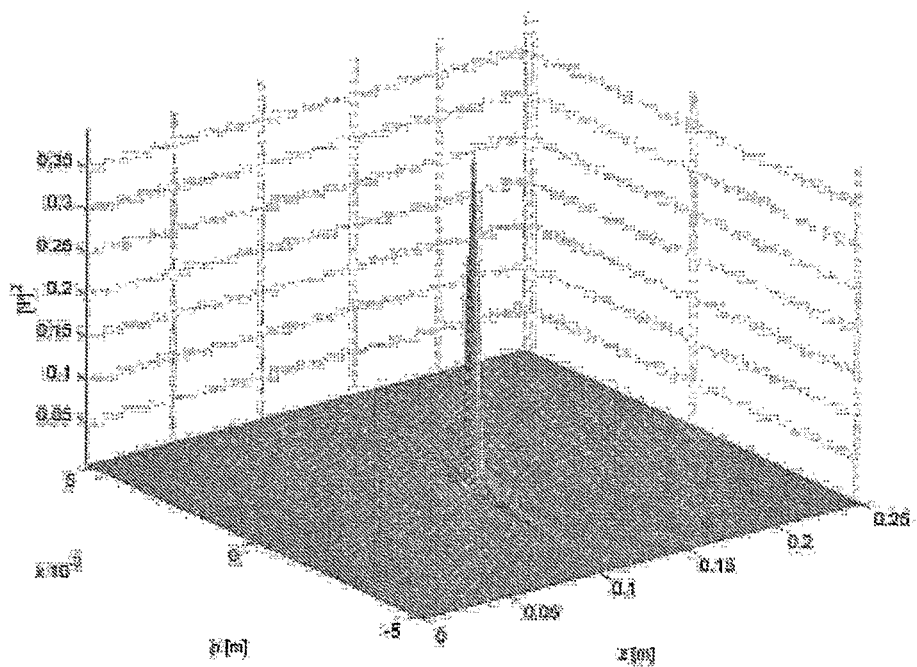
FIG. 32 is a 3D view of the localized stationary wave field represented in FIG. 31, obtained according to the invention by superposition of 181 Bessel beams, and corresponding to situation (4) in the following: i.e., to the acoustic case
Figure 33:
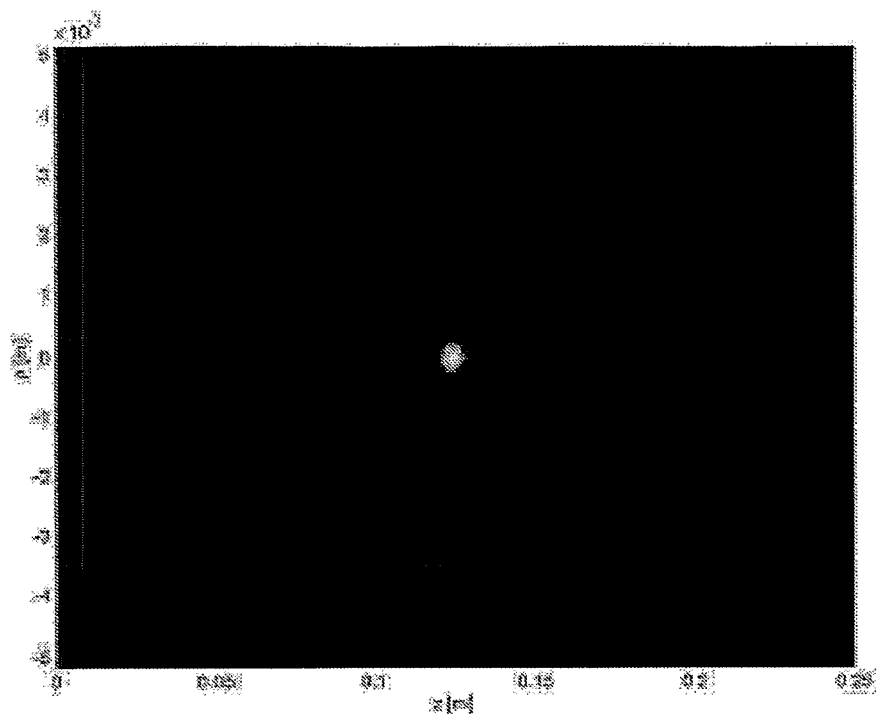
FIG. 33 is an orthogonal projection of FIG. 31.
Figure 34:
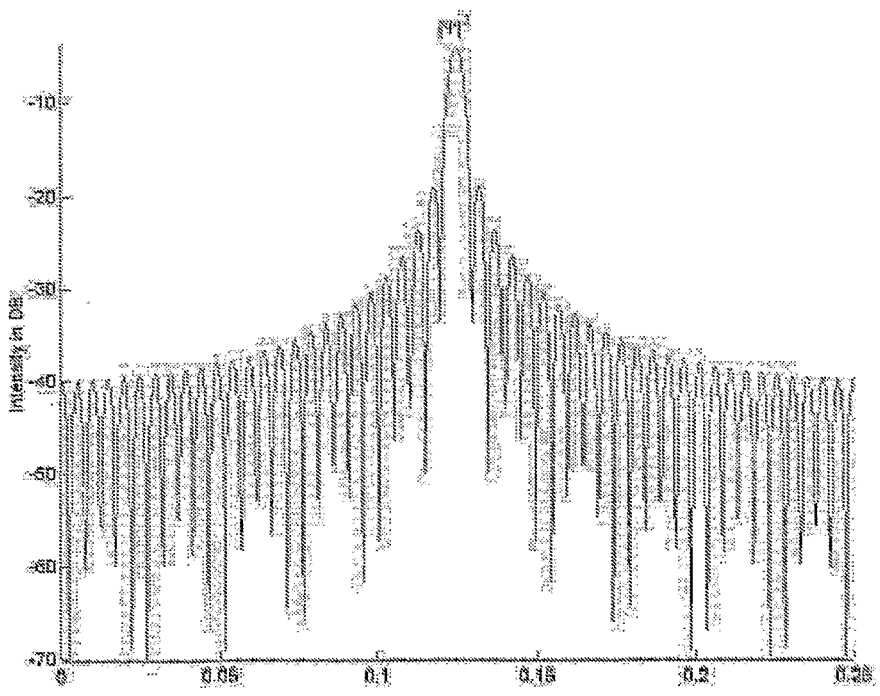
FIG. 34 illustrates FIG. 31 in DB units.
Figure 35:
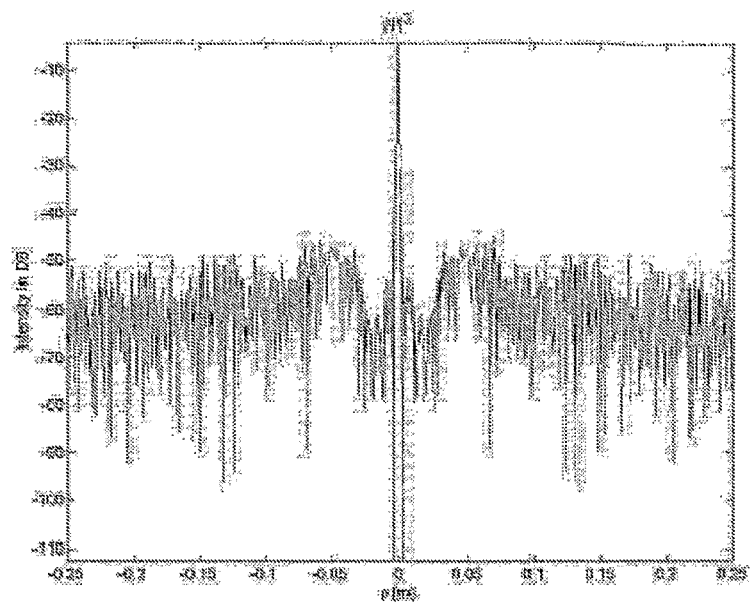
FIG. 35 illustrates the transverse behavior of the localized stationary wave fields corresponding to to FIGS. 31 to 34, in the plane $z=z_f$.

In FIGS. 31 to 34 the localized stationary wave field FW corresponding to this pattern is shown. FIG. 31 shows the 2D plot [again the line indicated by F(z) is the desired field, and the line indicated by FW is the localized stationary wave field actually obtained]. FIG. 31 shows the 3D representation of FIG. 31, and FIG. 33 is an orthogonal projection. In FIG. 34 we recast FIG. 31 in decibel, to show the residual intensity in a more clear way.

In this case the source can be manufactured by using discrete sources (transducers) located in the plane z=0 along a circular aperture of radius 6 cm, or by using again an array of annular slits. In the latter case, the radii of such annular slits must get values of centimeters, with an acoustical lens having focal length of 1 m and aperture radius of 6 cm (source size).

We can use 51 annular slits, with a minimum radius of 3.3 cm and a maximum radius of 8.7 cm. Other configurations would be possible too.

Consideration of the Use of the Method with Higher Order Bessel Beams Functions

Considering the use of higher order Bessel beams, an advanced method is disclosed.

Figure 36:
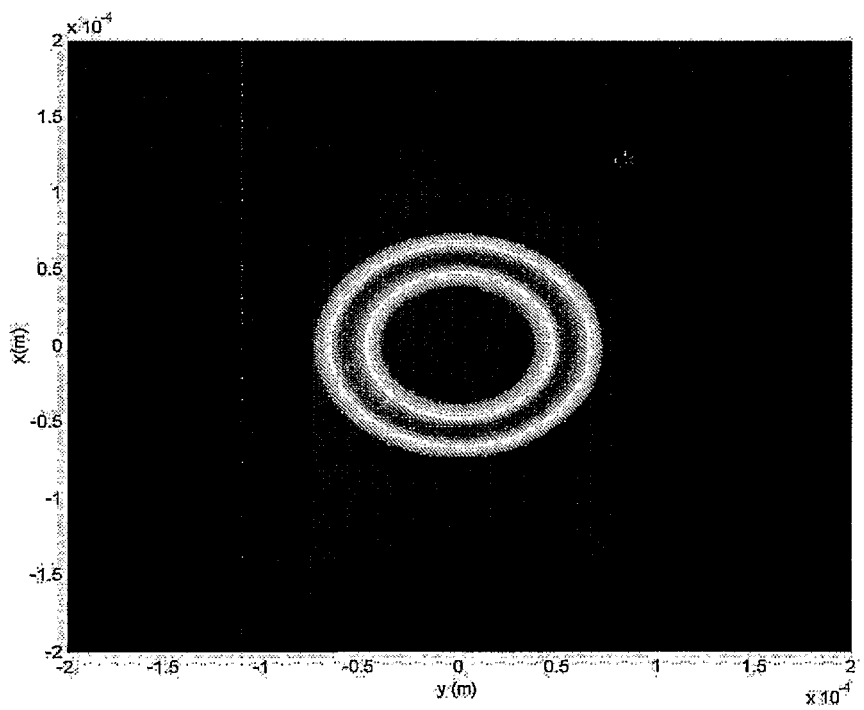
FIG. 36 illustrates the cross section of a stationary wave field according to the invention obtained by a superposition of Bessel beams of higher order.

According to the experience made up to now by the inventors, it is considered not a limitation, but rather a convenience, skipping the use of Bessel beams of order greater than fifth. Therefore, $1^{st}$, $2^{nd}$, $3^{rd}$, and $4^{th}$ order Bessel functions were used in attempts for concentrating energy along one or more rings (or on the surface of a cylinder) with center on the propagation axis and orthogonal to such an axis. Actually, the Bessel functions of order greater than zero possess zero intensity on the axis and circular pattern of intensity around the axis. The result of the application of the proposed method is the production of a cylindrically distributed power with a predefined intensity. This allows to produce, for instance, confining fields to be used (as an example) for confining particles during their motion (without any need of having a surrounding or inner field generator Such a type of confinement can act even on neutral particles or objects, due to the impulse transferred by the intense field. FIG. 36 illustrates the cross-section of such a Stationary wave field.

It is also possible to use in conjunction two emitters: one using zero-order Bessel beams, and the other using higher order Bessel beams, so, for example, to shield the action of external fields on the inner one. This can be particularly useful in systems very sensitive to electromagnetic perturbations, such as plasma fields. The above-mentioned application of the method allows also designing a transducer, able to produce a field for confining a plasma, when the typical problem is to contrast the radiation pressure that moves ions, particle and molecules from the hotter to the colder regions. In this case the stationary wave field produced by superposing higher order Bessel beams should be at least shaped as a cylindrical surface Consideration of the Various Methods and Devices to Control Phase and Amplitude of the Superposed Beams Embodiments I) According to the disclosed method, each of the emitting elements of the antenna is characterized by its Transfer function. As already mentioned, in the case of optical (annular, etc.) slits, each slit may be covered by a proper super-thin film, in order to control amplitude and phase of the emitted (Bessel, etc.) beam. The process for obtaining this thin film is sometimes complicated or costly, and it is here disclosed that an alternative simple, cheap solution consists in using a series of lenses. In specific applications similar to the mentioned (optical) one, just one suitable lens can be added: Such a lens (equal to the first one, that was located in such a way that the antenna falls in its rear focal plane) has to be designed and placed just after the slits, thus producing the proper phase shifts and reducing to an easier problem the amplitude control of the generated beams. And more in general of its transfer function From the description of the above cases, it has become clear that alternative setups can be provided for constructing a source capable of generating a localized stationary wave field of the kind according to the present invention. Let us also recall that other forms of generation can be used, for example by holographic elements, axicons, and by discretized antennas of the type discussed hereinafter.

Namely, according to an alternative embodiment of a source for generating a localized stationary wave field with the method of the present invention, a field behaviour corresponding to the superposition of Bessel beams (leading to the said stationary localized wave field) can be achieved by using a series of spot-like emitters, so to produce an effect similar to the one produced by axially symmetric emitters. In such a case, the spot-like emitters can be either ceramic ultrasound generating spots (in acoustics), or micro and nano dipoles, photonic spots, macro, micro and nano grids (in optics or microwaves, etc.), and other similar emitters.

The superposition effect is obtained by exciting each of the spot-like generators with an appropriate phase and intensity, in order to have a global superposition effect similar to the one produced by rings. The advantage of this composed transducer is the capability to be properly tuned, in case of a non-uniform medium, by using e.g. feedback system on echoed/transmitted signals.

The method and apparatus according to the present invention can be applied to (or can provide) many different specific treatment methods, and many specific devices or tools.

Figure 37:
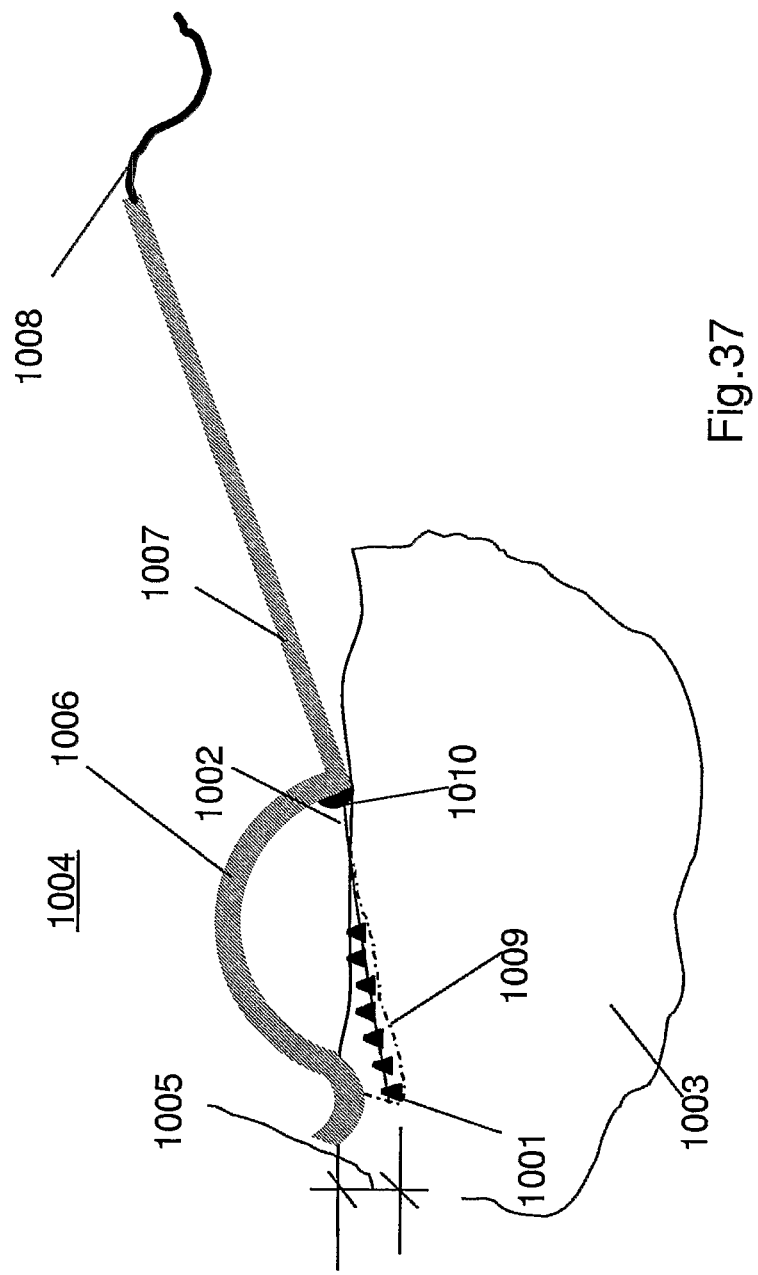
FIG. 37 illustrates schematically an embodiment of a laser cutting device operating according to the method of the present invention.

In a first specification of the present embodiment of the invention, an optical or laser cutting device is generated by the concentration of laser waves at one point, or in a series of points. The aim is to have a segment constructed by spots of high intensity field. FIG. 37 illustrates a schematic example of such a laser cutting device. In FIG. 37 the reference number 1003 indicates a body to be submitted to the cutting action, while the external environment is indicated with 1004. A high energy laser emitter or a high energy ultrasound transducer 1010 is placed at an end of a rod-like handle 1007. The laser emitter or the ultrasound transducer is energized by means of a supply means 1008 which is guided to the emitter/transducer 1010 through the handle 1007. The emitter/transducer 1010 is supported at an end of the handle 1007 in such a way that the line of filed projection indicated by the dotted line 1002 in FIG. 37 is at least approximately oriented in the axial direction of the handle 1007. The emitter/transducer is enclosed on the side of the environment surrounding the object to be cut by a cup shaped head 1006. This cup-shaped head 1006 has a rounded edge at the zone opposite to the emitter/transducer, enabling a simpler sliding of the head on the surface of the object on which the cutting action is carried out. The triangular black dots indicate by the numeral 1009 indicates the cutting or separation line. In prior art, optical or laser cutting tools are known, also as surgical beams for example, but the present invention is able to produce a more intense field than by the known devices with the same energy input. Moreover the region interested by the field is very limited and sharply defined, and can be controlled with a very high precision. Due to the capacity of the localized stationary wave fields according to the present invention to concentrate the whole energy inside a confined volume of predetermined dimension and shape, while reducing to a negligible level the energy spread outside the said volume This is particularly important when considering a surgical cutting tool, or similar devices, since no disturbance or modification is produced in the tissues or material before and after the high-field region (where the cutting action has to be carried out).

II) A second preferred embodiment of the present invention is the generation of optical or electromagnetic tweezers, useful for microscopic manipulation such as DNA cutting or even single particle capturing. Actually, in previous art some tools of this type are known, but there is no skilled approaches—for instance—for confining a particle (even neutral, due to exchange of mechanical impulse with the photons of the stationary field) with the precision reachable by the use of the antennas, in particular transducers, designed according to the method of the present invention. The use of Bessel beams is well-known, but the generation of a proper superimposition of Bessel beams in order to create a stationary wave field (able for instance to exchange mechanical impulse with the particle) is one of the novel applications of the mentioned new type of tweezers.

III) A further preferred embodiment refers to optical microlithography. In previous art, Bessel beams are used in such a field to produce pattern for successive etchings, but there is a limit in controlling with precision the etching positioning. By using the present method, an antenna, i.e. a source (in particular, a transducer) can be determined in order to get a predefined precision, that is limited by the wave dimensions only, thus increasing dramatically the etching depth resolution, besides its transverse resolution.

IV) Still another preferred embodiment of the present invention is the generation of electromagnetic (or acoustic) "balls", so to be able to transmit power from a location to another with minimum losses. This is further favoured by the property of each Bessel beam, constructing by interference the stationary "ball", of rebuilding its own shape after an obstacle. When the obstacle dimensions are smaller than the size of the lens (belonging to the antenna/transducer), each of the beams bypasses any obstacle on its route, recomposing finally the stationary field. One of the results is a reduced sensitivity to environmental perturbation. It must be recalled, at this point, also that, inside the 3D envelope (or envelopes) constituting the FW, there is a propagating carrier wave, i.e., a propagating plave wave given by $\exp[iQz-(\omega_0)t]$.

V) Still another preferred embodiment of the present invention is an apparatus for a new kind of "tele-communications". The method allows designing an antenna/transducer, able to create a stationary field envelope at a first space position only, which will not be detectable, of course, at a second, different position If the position of the desired receiver is known with good approximation, it is possible to design the transducer in order to generate a positive superimposition of the composing Bessel beams in that specified region of space only VI) Still another preferred embodiment of the present invention is a new kind of flexible holography, i.e., the generation of a three-dimensional image through the accurate phase tuning of the Bessel (or other) superposed beams. To this purpose, an antenna, or transducer, is disclosed (using, e.g., MEMS, piezoelectric effects, thermal effects, . . . ) able to modify the rings for example modifying the radii or even the thickness, in a coordinated; way together with the phase of the composing Bessel (or other) beams coming from the multi-channel generator. In such a way, a three-dimensional image can be generated without the need of ordinary holographic technology. Moreover, such a three-dimensional image could be moved around by such antenna/transducer, even changing its shape in time, resulting in a much better flexibility of the "holographic" arrangement VII) Another preferred embodiment of the disclosed method is the design of a sound region, limited in space. This allows generating an area of sound not propagating outside it. A transducer is described, able to produce such an effect. The effect is useful for replacing earphones with an immaterial earphone by creating, "projecting" the sound from the special transducer. In this case as already disclosed in a more general case, a spatially confined and stationary envelope of an acoustic field can be generated by means of the method according to the present invention. While inside the envelope acoustic beams can generate the acoustic sounds Embodiments in the Sector of Therapeutic or Diagnostic Treatments or Methods in Medicine Particular attention is to be given to the use of the method according to the present invention in the field of therapeutic or diagnostic treatments or methods, and of the corresponding tools.

In the medical field, applications for cancer treatment, calculosis destruction, thermal therapies have been investigated and analysed, in order also to describe advantages of the use of the present method compared with the existing ones. Moreover, technical considerations based on the use of the disclosed method permit the design of complete new therapies, and an improvement of existing ones.

The characteristics of the stationary field (FW), cited above, due to the present invention are principally, but not exclusively:
Residual Intensity
Spatial Resolution
Minimum Distance from a source generating the localized field ("Frozen Waves")
Source Size
Penetration Depth of the Frozen Waves For medical purposes, the method of the localized stationary wave fields, according to the present invention, would a priori yield more useful results for high frequency electromagnetic/optical or acoustics fields. In fact, with high frequencies, it is possible to deal with smaller sources and higher spatial resolution. We could think even about Gamma or X rays applications.

Practical examples of the use of the present invention in therapy and diagnostic and for providing new therapeutic and diagnostic devices are described in more detail in the following:

VIII) According to a first embodiment (for this new sector) of the use of localized stationary wave field due to the present invention in the sector of medicine, an apparatus able to destroy tumours is provided, which carries out its action on the tumoral mass by irradiating it with (intense) localized, strationary energy.

In the prior art, there are several transducers and methods for similar functions, but they are all affected by the negative characteristic of irradiating also the intermediate tissues located before and after the tumour, thus reducing drastically the time for each irradiation and elongating the therapeutic cycle, besides all the other known negative side effects. The use of electromagnetic waves is difficult since it is easy to concentrate high (localized, stationary) energy inside a small spot via microwaves, i.e., short wavelength (e.g., few millimeters) waves: But such waves hardly penetrate beyond the skin, so this technique and apparatus could be suitable only for superficial diseases.

By contrast, 300-500 MHz, till about 1 GHz, waves (endowed with wavelength of almost 1 m) are able to penetrate the human body. Concentrating these long waves into a limited region can be possible only by using antennas of a few meters diameters with a focal length not less than some meters, confining their use in important therapeutic treatments, according to the literature of the area. Anyway, the present invention allows concentrating enough such short or long electromagnetic waves, to use them for curing tumours.

According to an alternative embodiment the said device could be also used as image transducers and/or receivers capturing transmission or reflection beams, to detect and record the position of significant biological features such as tumors, with the possibility of avoiding the use of ionizing radiation or intense magnetic fields.

IX) Another preferred embodiment of the present invention in the medical field consists in an apparatus able to destroy tumours by using ultrasounds. Similar devices are well known in the area, using multiple patterns or a variable pattern to concentrate the ultrasound on a defined target, while trying to reduce the amount of residual dose on the surrounding tissues. In the disclosed embodiment, the transducer designed according to the abovementioned method allows to generate an extremely high concentration of ultrasound on the target, or rather inside a predetermined spatial-region (spot), and a really negligible effect on the material before or after or surrounding the target, to the superimposition of proper Bessel (or other) beams according to the present invention.

A multi-transducer generates a sound field by superimposition of acoustic Bessel (or other) beams, according to the method, thus producing a high power acoustic field inside a very limited volume, of the order, e.g., of one cubic millimetre or much less. This allows destroying tumour masses without damaging tissues before or after or surrounding the focusing area.

X) Another similar preferred embodiment of the disclosed method is a method and an apparatus for the destruction of calculosis (e.g., kidney stones) by the mechanical action of stationary acoustic waves in the calculus volume. This is an advantage compared to prior art, since in the prior art devices a similar action is performed, but the area of intense field is not defined precisely as in an apparatus using a localized stationary wave field according to the present invention, so that in the prior art devices the surrounding tissue is damaged.

Figures 38A, 38B:
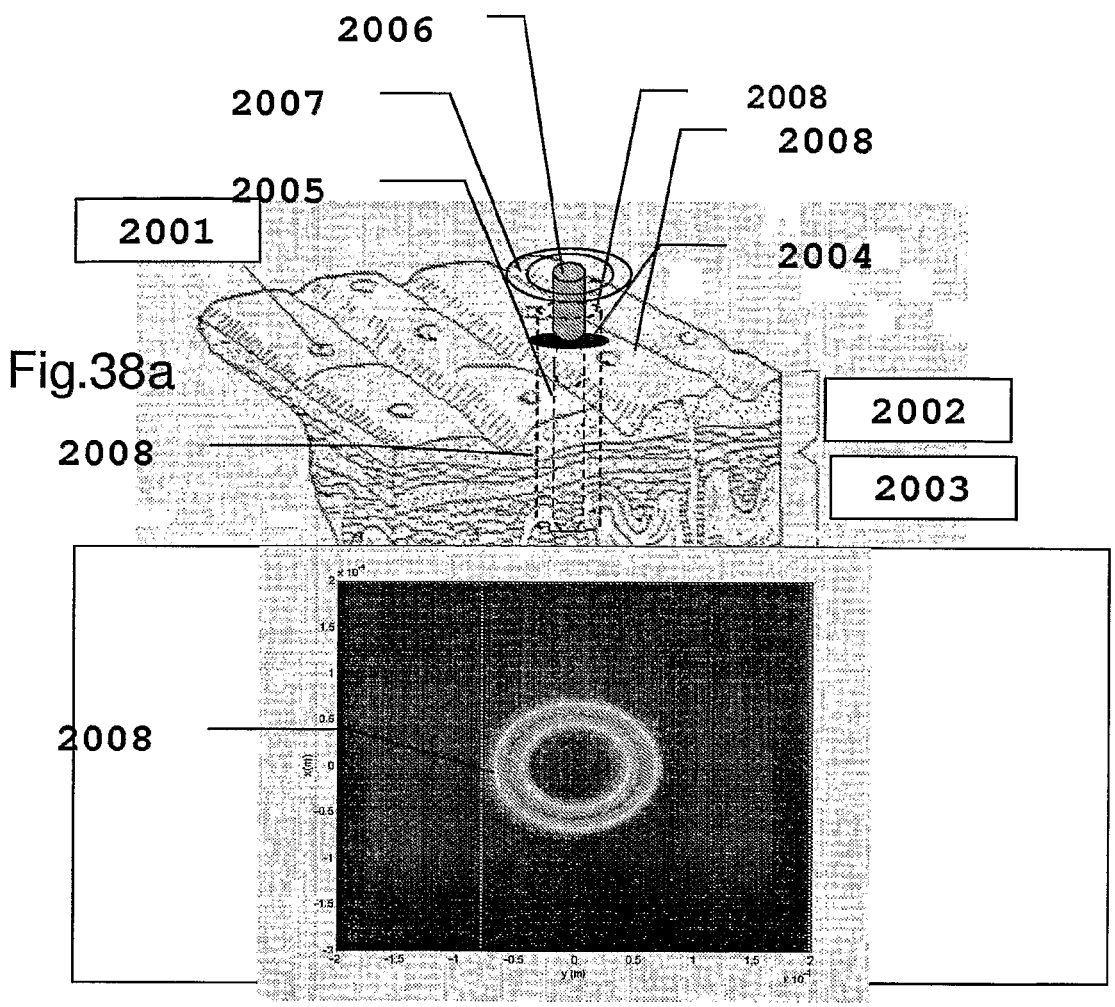
FIGS. 38a and 38b illustrates respectively a device for performing needle-less injections by applying the teachings according to the present invention.

XI) Another preferred embodiment of the disclosed method is the capability of performing needle-less injections of medicines and liquids, by using a highly concentrated sound or ultrasound field, with a predetermined shape. The "needle" can be actually generated in the form of an intense stationary field extending from above to below the patient skin (with a predetermined penetration depth also inside the patient body). A dose of medicine is laid on the skin and the field is alternatively switched on and off. This produces the passage of a small quantity of material from the dose through the skin. Repeating the cycle it is possible to introduce and disperse high quantity of medicines in the desired area/volume, in order to optimize adsorption and therapy FIGS. 38a and 38b illustrates respectively a device for performing needle-less injections by applying the teachings according to the present invention. In the percpective view of FIG. 38a a portion of dermis 2002 and epidermis 2003 is shown. As reference to the dimensions of the needle-less device disclosed the pores structure 2001 is also illustrated. A first acoustic or mechanical field emitter 2006, such as for example an ultrasound transducer, is placed at the external surface of the dermis at the point at which injection has to be carried out. At this point or zone a drop 2004 of medicine compound is deposited. The first transducer 2006 generates a field having a stationary and spatially localized envelope with inner moving wave fronts which oushes the medicine or compound 2004 through the dermis and epidermis 2002, 2003. The stationary and spatially localized envelope of the field generated and extending through the dermis and epidermis 2004 is illustrated with dotted lines and is indicated with the reference numeral 2005. A further secondary emitter, particularly an ultrasound transducer 2007 is provided. This emitter/transducer 2007 is of annular form and generates a cylindrical tubular, additional containment field 2008. The transversal intensity pattern of the said tubular additional containment field is illustrated in FIG. 38b. Such a kind of field having a stationary spatially confined envelope can be obtained according to the present invention by using superpositions of higher order waves, particularly of Bessel beams, than zero order waves or Bessel beams.

Figure 39:
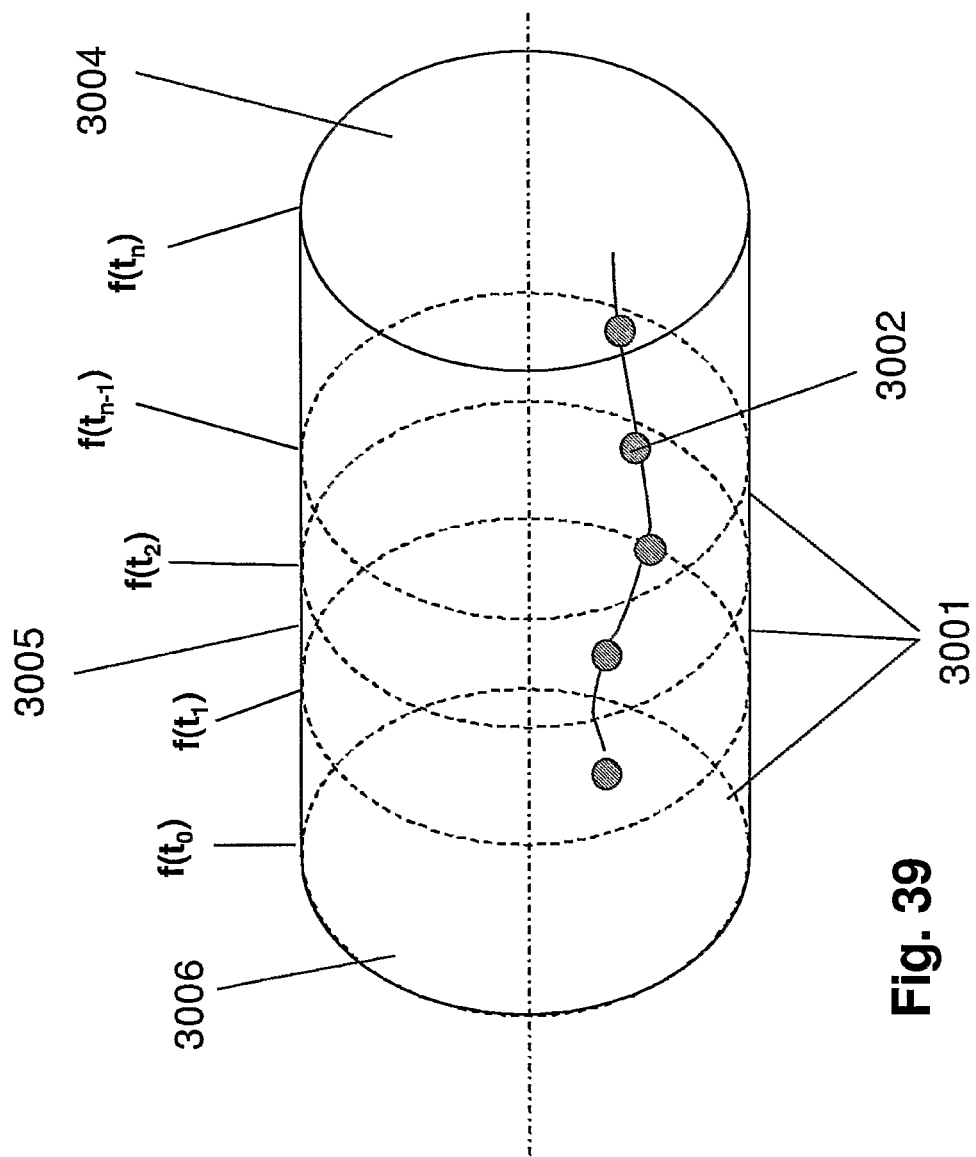
FIG. 39 is a schematic figure illustrating the case where inside a stationary envelope or sub-envelopes any kind of propagating wave can be generated and not only a plane wave: for example in such a way to generate a peak which is born on a first side of the envelop or sub-envelope and dies on the other side of the said envelope or sub envelope, while a second peak appears on the said first side.

Referring to FIG. 39 therein there is illustrated the case where inside a stationary envelope or sub-envelopes any kind of propagating wave can be generated and not only a plane wave: for example in such a way to generate a peak which is born on a first side of the envelop or sub-envelope and dies on the other side of the said envelope or sub envelope, while a second peak appears on the said first side. The dotted circles 3001 indicate a wavefront inside the stationary localized envelope which borders are indicated by the continuous lines 3003, 3004 and 3005. with numerals 3002 a particle, a drop or a cell it any kind of object is indicate which interacts with the wave front. The wave front is borne on the left side and dies on the right side of the envelope, namely respectively at 3003 and 3004, while it is transversally confined by the envelope borders 3005.

It has to be noticed that, although the present method has been described with reference to a superposition of Bessel beams, other kinds of beams can be used. Particularly suited beams are the ones having an high transverse confinement. This leads to a high transverse concentration of the energy. In particular, beams can be used whose crosssection is not circular but elliptical, or whose transverse energy distribution is represented by other functions having at least one high narrow peak (centered on the propagation axis, or elsewhere: e.g., along a circumference surrounding the z-axis) decreasing to negligible amplitudes.

In the present description and in the claims the definition "Bessel beams" will be understood as comprising any kind of other beams suitable for carrying out the method according to the invention.

Deeper details of the theoretical scientific background of the present invention are disclosed in the following references which are part of the present description:

J.-Y. Lu and J. F. Greenleaf: "Experimental verification of nondiffracting X-waves", IEEE Trans. Ultrason. Ferroelectr. Freq. Control, vol. 39 (1992) pp. 441-446.

E. Recami: "On localized 'X-shaped' Superluminal solutions to Maxwell equations": Physica, vol. A252 (1998) pp. 586-610.

M. Z. Rached, E. Recami, and H. E. Harnandez F.: "New localized Superluminal solutions to the wave equations with finite total energies and arbitrary frequencies", Europ. Phys. J., vol. D21 (2002) pp. 217-228.

E. Recami, M. Z. Rached, K. Z. Nobrega, C. A. Dartora, and H. E. Hernandez F.: "On the localized superluminal solutions to the Maxwell equations" IEEE J. Sel. Top. Quantum Electronics, vol. 9(1) (2003) pp. 59-73.

M. Z. Rached, K. Z. Nobrega, H. E. Hernandez-F., and E. Recami: "Localized Superluminal solutions to the wave equation in (vacuum or) dispersive media, for arbitrary frequencies and with adjustable bandwidth", Opt. Commun., vol. 226 (2003) pp. 15-23.

M. Z. Rached, A. Shaarawi, and E. Recami: "Focused X-shaped pulses", in press in J. Opt. Soc. Am., vol. A21 (August, 2004).

The invention claimed is:

1. A method of producing a stationary localized wave field of an a-priori predetermined arbitrary shape comprising the following steps:
   providing a laser emitter or ultrasound transducer generating a beam;
   defining at least a volume limited in the direction of an axis z of propagation of the beam, the volume being a longitudinal interval having $0 \leq z \leq L$, where z is a longitudinal position and L is a length of a longitudinal interval;
   defining a priori within the longitudinal interval an intensity pattern $\mu f(z) \mu^2$ describing a desired localized and stationary wave field, where $\mu$ is a cylindrical coordinate and F(z) is a function, the function F(z) being represented by a discrete Fourier Series or by another expansion based on a trigonometric orthogonal functions;
   providing a discrete, generic superposition of Bessel beams or other transversally confined beams;
   calculating a maximum allowed number of Bessel beams to be superposed;
   calculating amplitudes, phase velocities, and transverse and longitudinal wavenumbers of each Bessel beam or other transversally confined beam of the superposition, needed to obtain a predefined STATIONARY intensity pattern within the longitudinal interval; and
   recognizing and controlling an effect of each of the amplitudes, phase velocities, and transverse and longitudinal wavenumbers in the step of calculating amplitudes for controlling a longitudinal shape of the stationary localized wave field,
   thereby generating a source of the desired localized and stationary wave field having an a-priori predetermined arbitrary shape.

2. The method according to claim 1, in which the Bessel beams or the transversally confined beams have the same frequency.

3. The method according to claim 1, wherein the Bessel beams or the transversally confined beams have different frequencies.

4. The method according to claim 1, wherein the Bessel beams or the transversally confined beams have a certain bandwith.

5. The method according to claim 1, wherein the Bessel beams or the transversally confined beams are pulsed.

6. The method according to claim 1, wherein the Fourier expansion defining the intensity pattern within the longitudinal interval is a trigonometric expansion.

7. The method according to claim 6, wherein the Fourier expansion defining the intensity pattern within the longitudinal interval is a Fourier series.

8. The method according to claim 1, wherein the generic superposition of Bessel or the other transversally confined beam is provided by the following function:

$$\Psi(\rho, z, t) = e^{-i\omega_0 t} \sum_{n=-N}^{N} A_n J_0(k_{\rho n}\rho) e^{i\beta_n z} \quad (5)$$

where $\rho$ is a three-dimensional polar coordinate, i is a complex number, $\omega$ is a Bessel beam, J is a Bessel function, n are integer numbers, $A_n$ is a constant coefficient, $\beta_n$, $k_{\rho n}$ are the longitudinal and transverse wavenumbers, $\mu_0$ is a frequency, $\mu$, z are cylindrical coordinates, and t is time, wherein in equation (5), for each n the parameters $\omega_0$, $k_{\rho n}$, $\beta_n$ must satisfy the condition $$k_\rho^2 = \frac{\omega^2}{c^2} - \beta^2 \geq 0 \quad (3)$$

where $\beta$ is a longitudinal wavenumber expressed as a continuous function, and the intensity pattern in correspondence of a predefined delimited longitudinal interval, defined as $0 \leq z \leq L$, is given by the following Fourier series:

$$F(z) = \sum_{m=-\infty}^{\infty} \left( B_m e^{i\frac{2\pi}{L}mz} \right) \quad (7)$$

where m is a step function and $$B_m = \frac{1}{L} \int_0^L F(z) e^{-i\frac{2\pi}{L}mz} dz; \quad (8)$$

wherein a specific superposition of the Bessel or other transversally confined beams needed for obtaining at least approximately the defined intensity pattern within the chosen longitudinal interval is defined by the following function:

$$\Psi(\rho=0, z, t) = e^{-i\omega_0 t} e^{iQz} \sum_{n=-N}^{N} A_n e^{i\frac{2\pi}{L}nz} \quad (11)$$

with amplitudes $A_n$ given by $$A_n = \frac{1}{L} \int_0^L F(z) e^{-i\frac{2\pi}{L}nz} dz \quad (12)$$

the maximum number N of superimposed Bessel or other transversally confined beams being defined by $$0 \leq Q \pm \frac{2\pi}{L} N \leq \frac{\omega_0}{c} \quad (10)$$

where the longitudinal wavenumbers are defined by $$\beta_n = Q + \frac{2\pi}{L} n \quad (9)$$

and where Q is an empiric selectable parameter provided that:
$0 < Q < (\omega_0)/c$; and where α represents an attenuation coefficient and L is a length of the considered longitudinal interval.

9. The method according to claim 8, wherein cylindrical coordinate p is different from zero, such that the superposition of the Bessel beams for obtaining the desired intensity pattern in correspondence with the considered longitudinal interval is given by $$\Psi(\rho, z, t) = e^{-i\omega_0 t} e^{iQz} \sum_{n=-N}^{N} A_n J_0(k_{\rho n}\rho) e^{i\frac{2\pi}{L}nz} \quad (13)$$

with $$k_{\rho n}^2 = \omega_0^2 - \left(Q + \frac{2\pi n}{L}\right)^2. \quad (14)$$

10. The method according to claim 1, wherein the function F(z) describing the intensity pattern within the longitudinal interval is a one step function or a combination of step functions.

11. The method according to claim 10, wherein the function F(z) is a function piecewise continuous in the interval $0 \leq z \leq L$.

12. The method according to claim 1, wherein the Bessel beams are mechanical wave beams including seismic and geophysical waves.

13. The method according to claim 12, wherein the mechanical wave beams are acoustic waves.

14. The method according to claim 1, wherein the Bessel beams are electromagnetic wave beams.

15. The method according to claim 1, wherein the stationary wave field is an electric field.

16. The method according to claim 1, wherein the stationary wave field is a magnetic field.

17. The method according to claim 1, wherein the Bessel beams are gravitational wave beams.

18. The method according to claim 1, wherein the Bessel beams are wave beams representing fundamental particles.

19. The method according to claim 1, wherein more than one longitudinal interval is provided, wherein a stationary wave field is present, wherein more than one longitudinal intervals are defined and the function F(z) is provided for describing the wave field intensity pattern corresponding to more than one longitudinal intervals, the longitudinal intervals being at a desired distance one from the other, and wherein the steps of claim 1 are carried out by applying the function F(z).

20. The method according to claim 1, wherein the Bessel beams of the superposition of Bessel beams are zero order Bessel beams.

21. The method according to claim 1, wherein at least a part of the superposition of Bessel beams further comprises higher-order Bessel beams than zero order Bessel beams.

22. The method according to claim 1, wherein all or some of the Bessel beams of the superposition of Bessel beams are Bessel beams of higher order than zero order.

23. A source configured to produce a stationary wave field of arbitrary shape with the method according to claim 1 to comprising:
an array of Bessel or other beam sources having an high transverse confinement, each of the sources of the array being devoted to generation of a Bessel beam or other beam having different parameters of amplitude, phase, and longitudinal and transversal wavenumber; and
a system driving each of the sources of the array to generate a Bessel beam having frequency identical or different to the one of the other Bessel beams generated by the other sources of the array.

24. The source according to claim 23, wherein the array of the Bessel beam sources are in the form of a set of annular concentric or coaxial sources, each of the annular concentric or coaxial sources generating the Bessel beam with a defined amplitude, phase, longitudinal and transverse wavenumbers.

25. The source according to claim 23, wherein the source provides a superposition of the Bessel beams or other beams having an high transverse confinement for generating a stationary and confined electromagnetic wave field, the source comprising;
an initial generator of an electromagnetic beam, the electromagnetic beam being directed against an annular array of concentric annular slits having 2N+1 annular slits, each slit generating out of the impinging electromagnetic beam the Bessel or other beam endowed with a same frequency or with a different frequency as the other Bessel beams or other beams, the Bessel or other beam possessing characteristic amplitude and phase, and characteristic longitudinal and transverse wavenumbers; and
a lens on an output side of the array of annular concentric slits, such that the array is located at a focus of the lens, the slits having a radius defined for each n-th annular slit by the following expression:

$$\alpha_n = f\sqrt{1 - \frac{c^2}{\omega_0^2}\left(Q + \frac{2\pi}{L}n\right)^2}$$

where $\alpha_n$ is a weight of a Bessel beam generated by the n-th slit, c is light speed, $\omega_0$ is a Bessel beam with a same frequency, L is the extension of the longitudinal space interval corresponding to a confined space-region in which the wave field is created, f is a focal length of the lens, and Q is a positive constant contained in the interval $0 < Q < \alpha_0/c$;
a radial width of each annular slit being such that it obeys only the condition $\alpha_0 \ll \alpha_f/R$.

26. The source according to claim 23, wherein the source provides for a superposition of Bessel beams having equal frequency.

27. The source according to claim 23, wherein the source is configured to provide for acoustic, electromagnetic, gamma ray, X-ray, or ultrasound Bessel beams.

28. The source according to claim 23, further comprising:
at least one initial beam generator; and
at least one diffraction pattern against which an initial beam is directed, the diffraction pattern being formed by an array of coaxial annular slits, a Transfer Function and a radius of each annular slit being correlated with amplitude, phase and longitudinal and transverse wavenumbers of corresponding Bessel beams, the correlation being determined such to generate a superposition of the Bessel beams having a same frequency or different frequencies.

29. The source according to claim 28, further comprising an additional lens with a same focus f immediately after the array of coaxial annular slits, the additional lens making simpler a construction of the Transfer Function of the annular slits.

30. The source according to claim 23, wherein the source is formed by an array of spot emitters, and wherein a system driving or exciting selectively the spot emitter is configured to excite the spot emitters with a predetermined phase and intensity given by $$\psi(\rho, z, t) = e^{-i\omega_0 t} e^{iQz} \sum_{n=-N}^{N} A_n J_0(k_{\rho n}\rho) e^{i\frac{2\pi}{L}nz}, \quad (13)$$

where $\rho$ is a three-dimensional polar coordinate, z is a longitudinal position, t is time, i is a complex number, $\omega$ is a Bessel beam, $A_n$ is a constant coefficient, J is a Bessel function, n is an integer number, $k_{\rho n}$ is a transverse wavenumber, and L is a length of a longitudinal interval, to obtain a global superposition effect, similar but suitable to produce much more powerful stationary wave fields that the one of the superposition of Bessel beams defined with a method having the following steps:
  a) defining at least a volume limited in the direction of an axis z of propagation of a beam, the volume being a longitudinal interval having $0 \leq z \leq L$;
  b) defining a priori within the longitudinal interval an intensity pattern $\mu F(z) \mu^2$ describing a desired localized and stationary wave field, the function F(z) being represented by a discrete Fourier Series or by another expansion based on a trigonometric orthogonal functions;
  c) providing a discrete, generic superposition of Bessel beams or other transversally confined beams;
  d) calculating a maximum allowed number of Bessel beams to be superposed;
  e) calculating amplitudes, phase velocities, and transverse and longitudinal wavenumbers of each Bessel beam or other transversally confined beam of the superposition, needed to obtain a predefined STATIONARY intensity pattern within the longitudinal interval; and
  f) recognizing and controlling an effect of each of the amplitudes, phase velocities, and transverse and longitudinal wavenumbers in step e) for controlling a longitudinal shape of the stationary localized wave field.

31. A method according to claim 1, wherein Bessel beams or other beam having a transverse confinement of different order are provided in the superposition of Bessel beams or other beams having a transverse confinement, said beams being generated with the method according to claim 1, while transfer functions of annular slits act also as an angular modulator.

32. The source according to claim 30, wherein the spot emitters are ceramic or semiconductor-based ultrasound generating spot, micro or nano dipoles, photonic spots, macro, micro or nano grids.

33. A device comprising one or more of electromagnetic, optical, or acoustic tweezers comprising:
  a source configured to generate a stationary wave field at one or more predetermined spots in space, the source comprising:
    an array of Bessel or other beam sources having a high transverse confinement, each of the sources of the array being devoted to generation of a Bessel beam or other beam having different parameters of amplitude, phase, and longitudinal and transversal wavenumber; and
    a system driving each of the sources of the array to generate the Bessel beam having frequency identical or different to the one of the Bessel beams generated by the other sources of the array,
  wherein the stationary wave field is generated according to a method comprising the following steps:
    a) defining at least a volume limited in the direction of an axis z of propagation of a beam, the volume being a longitudinal interval having $0 \leq z \leq L$, where z is a longitudinal position and L is a length of a longitudinal interval;
    b) defining a priori within the longitudinal interval an intensity pattern $\mu F(z) \mu^2$, where $\mu$ is a cylindrical coordinate and F(z) is a function, describing a desired localized and stationary wave field, the function F(z) being represented by a discrete Fourier Series or by another expansion based on atrigonometric orthogonal functions;
    c) providing a discrete, generic superposition of Bessel beams or other transversally confined beams;
    d) calculating a maximum allowed number of Bessel beams to be superposed;
    e) calculating amplitudes, phase velocities, and transverse and longitudinal wavenumbers of each Bessel beam or other transversally confined beam of the superposition, needed to obtain a predefined STATIONARY intensity pattern within the longitudinal interval; and
    f) recognizing and controlling an effect of each of the amplitudes, phase velocities, and transverse and longitudinal wavenumbers in step e) for controlling a longitudinal shape of the stationary localized wave field.

* * * * *